United States Patent
Iwasaki et al.

(10) Patent No.: US 10,849,527 B2
(45) Date of Patent: Dec. 1, 2020

(54) MAGNETIC SENSOR, BIOLOGICAL CELL SENSING DEVICE, AND DIAGNOSTIC DEVICE

(71) Applicant: KABUSHIKI KAISHA TOSHIBA, Tokyo (JP)

(72) Inventors: Hitoshi Iwasaki, Tokyo (JP); Akira Kikitsu, Kanagawa (JP); Satoshi Shirotori, Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 602 days.

(21) Appl. No.: 15/698,372

(22) Filed: Sep. 7, 2017

(65) Prior Publication Data

US 2018/0271395 A1    Sep. 27, 2018

(30) Foreign Application Priority Data

Mar. 21, 2017  (JP) ................................ 2017-055133

(51) Int. Cl.
 *G01N 27/72* (2006.01)
 *A61B 5/05* (2006.01)
 (Continued)

(52) U.S. Cl.
 CPC .................. *A61B 5/05* (2013.01); *A61B 5/04* (2013.01); *A61B 5/04008* (2013.01);
 (Continued)

(58) Field of Classification Search
 CPC ......... A61B 5/05; A61B 5/04008; A61B 5/04; G01N 27/72; G01N 33/4833; H01S 4/00;
 (Continued)

(56) References Cited

U.S. PATENT DOCUMENTS

| 5,194,808 A | 3/1993 | Shintaku et al. |
| 7,755,936 B2 * | 7/2010 | Wecker ..................... G11C 5/02 365/171 |

(Continued)

FOREIGN PATENT DOCUMENTS

| JP | 7-113665 | 12/1995 |
| JP | H11-101861 A | 4/1999 |

(Continued)

OTHER PUBLICATIONS

Y. Majima et al., "AC Modulation Method of a TMR Magnetic Sensor", Okuyama Univ., MMM2016 FH06, The Magnetics Society of Japan, 2016, 6pB-3.

(Continued)

*Primary Examiner* — Son T Le
(74) *Attorney, Agent, or Firm* — Finnegan, Henderson, Farabow, Garrett & Dunner, L.L.P.

(57) ABSTRACT

According to one embodiment, a magnetic sensor includes a first sensor element and a first interconnect. The first sensor element includes a first magnetic layer, a first opposing magnetic layer, and a first nonmagnetic layer provided between the first magnetic layer and the first opposing magnetic layer. A first magnetization of the first magnetic layer is aligned with a first length direction crossing a first stacking direction from the first magnetic layer toward the first opposing magnetic layer. At least a portion of the first interconnect extends along the first length direction. The first interconnect cross direction crosses the first length direction and is from the first sensor element toward the portion of the first interconnect. A first electrical resistance of the first sensor element changes according to an alternating current flowing in the first interconnect and a sensed magnetic field applied to the first sensor element.

18 Claims, 13 Drawing Sheets

(51) Int. Cl.
*A61B 5/04* (2006.01)
*G01N 33/483* (2006.01)
A61K 49/00 (2006.01)
H01S 4/00 (2006.01)

(52) U.S. Cl.
CPC ......... *G01N 27/72* (2013.01); *G01N 33/4833* (2013.01); *A61K 49/00* (2013.01); *H01S 4/00* (2013.01)

(58) Field of Classification Search
CPC ........ A61K 49/00; G01D 5/16; H04L 47/805; H04L 47/781; H04L 47/72; H04L 47/525; H04L 47/6215; G01R 33/093; G01R 33/09; G01R 33/02; G01R 33/096; G01B 7/30

See application file for complete search history.

(56) References Cited

U.S. PATENT DOCUMENTS

| 2009/0015252 | A1* | 1/2009 | Raberg ................. B82Y 25/00 324/252 |
| 2013/0113478 | A1 | 5/2013 | Pant |
| 2013/0242435 | A1* | 9/2013 | Fuji ...................... G01R 33/093 360/244 |
| 2013/0337497 | A1 | 12/2013 | Hayden et al. |
| 2015/0082919 | A1* | 3/2015 | Higashi ................ H04R 19/005 73/862.69 |
| 2016/0163431 | A1* | 6/2016 | Zhou ....................... H01L 43/08 338/32 R |
| 2017/0363606 | A1 | 12/2017 | Kikitsu et al. |

FOREIGN PATENT DOCUMENTS

| JP | 2000-55999 A | 2/2000 |
| JP | 3705702 | 10/2005 |
| JP | 2013-137301 | 7/2013 |
| JP | 2014-509398 A | 4/2014 |
| JP | 2017-3336 | 1/2017 |
| JP | 2017-223570 A | 12/2017 |
| JP | 2018-48832 A | 3/2018 |
| JP | 2018-146314 A | 9/2018 |

OTHER PUBLICATIONS

Sining Mao et al., "Vertical GMR Recording Heads for 100 Gb/in", IEEE Transactions on Magnetics, vol. 39, No. 5, Sep. 2003, pp. 2396-2396.

P. Ripka et al., "AC-Driven AMR and GMR Magnetoresistors", Sensors and Actuators 76 (1999) pp. 225-230.

Robert Lamberton et al., "Current-in-Plane GMR Trilayer Head Design for Hard-Disk Drives: Characterization and Extendibility", IEEE Transactions on Magnetics, vol. 43, No. 2, Feb. 2007, pp. 645-650.

Michael A. Seigler, "Current-in-Plane Giant Magnetoresistance Sensor Using a Thin Cu Spacer and Dual Nano-Oxide Layers With a DR Greater Than 20 Ohms/sq", IEEE Transactions on Magnetics, vol. 43, No. 2, Feb. 2007, pp. 651-656.

* cited by examiner

|  | DM1 | D21 | L1(μm) | L2(μm) | Hc(Oe) | Hs(Oe) |
|---|---|---|---|---|---|---|
| SP11 | X | X | 500 | 10 | 0.2 | 30 |
| SP12 | X | X | 250 | 10 | 0.15 | 30 |
| SP13 | X | X | 100 | 5 | 0.1 | 40 |
| SP14 | X | X | 20 | 2 | 0.25 | 45 |
| SP15 | X | X | 20 | 1 | 0.2 | 50 |
| SP21 | Y | X | 250 | 10 | 3 | 19 |
| SP22 | Y | X | 100 | 5 | 4 | 22 |
| SP23 | Y | X | 20 | 2 | 5 | 25 |
| SP24 | Y | X | 20 | 1 | 2 | 32 |
| SP31 | X | Y | 250 | 10 | 14 | 25 |
| SP32 | X | Y | 100 | 5 | 11 | 25 |
| SP33 | X | Y | 20 | 2 | 17 | 25 |
| SP34 | X | Y | 20 | 1 | 15 | 25 |
| SP41 | Y | Y | 250 | 10 | 1.5 | 30 |
| SP42 | Y | Y | 100 | 5 | 3.5 | 40 |
| SP43 | Y | Y | 20 | 2 | 7 | 45 |
| SP44 | Y | Y | 20 | 1 | 12 | 50 |

FIG. 4

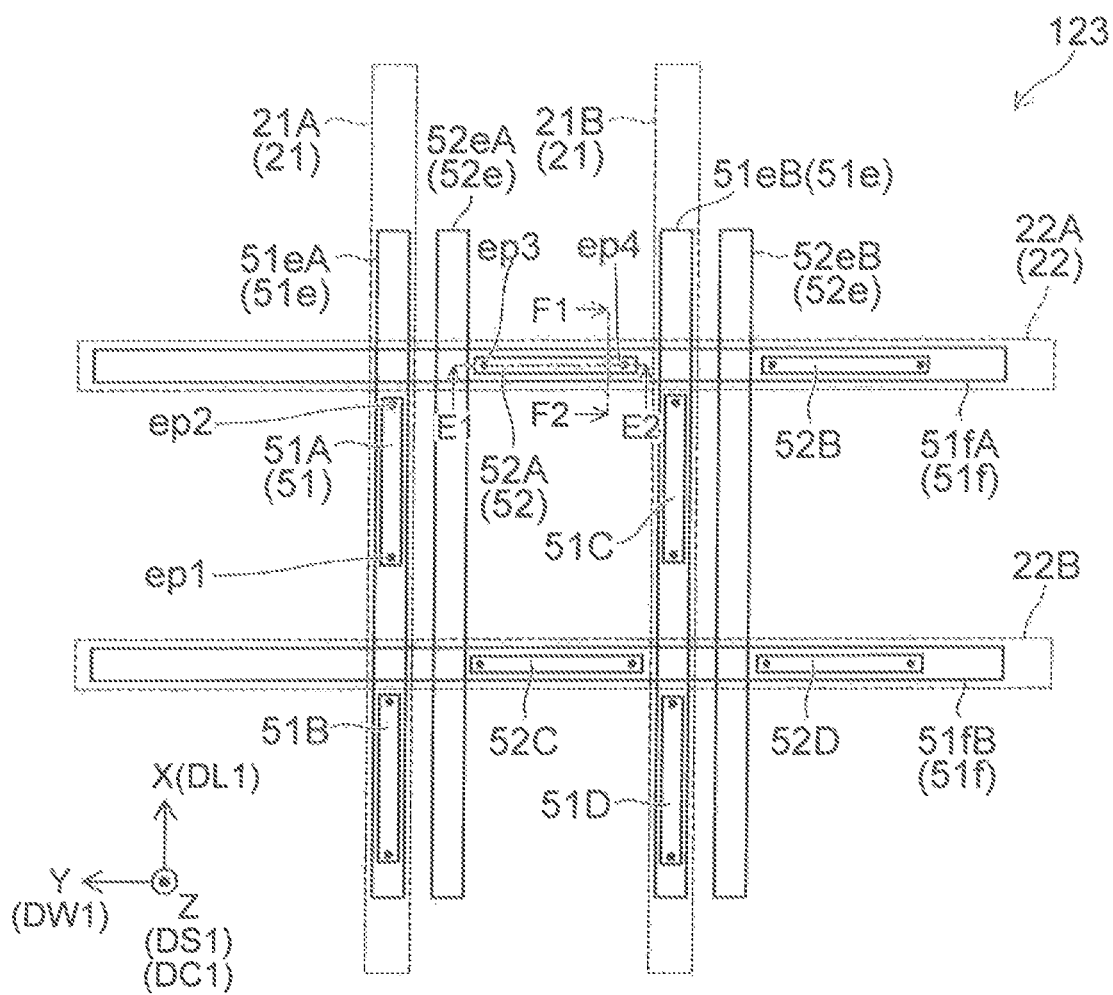
FIG. 11A
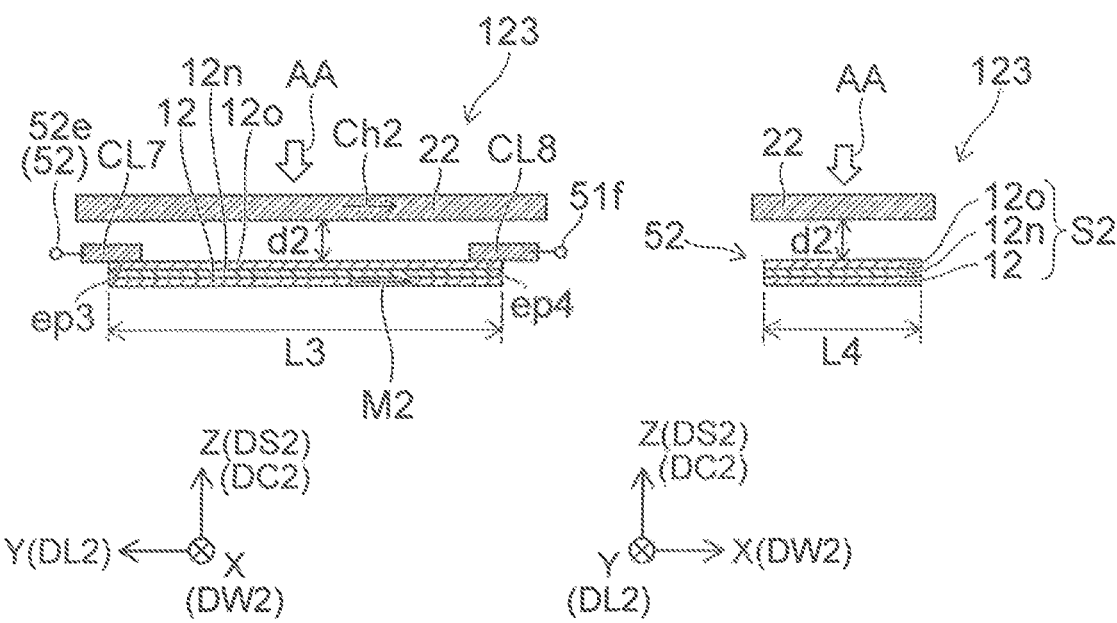
FIG. 11B
FIG. 11C

MAGNETIC SENSOR, BIOLOGICAL CELL SENSING DEVICE, AND DIAGNOSTIC DEVICE

CROSS-REFERENCE TO RELATED APPLICATIONS

This application is based upon and claims the benefit of priority from Japanese Patent Application No. 2017-055133, filed on Mar. 21, 2017; the entire contents of which are incorporated herein by reference.

FIELD

Embodiments described herein relate generally to a magnetic sensor, a biological cell sensing device, and a diagnostic device.

BACKGROUND

There is a magnetic sensor that uses a magnetic layer. It is desirable to increase the sensing sensitivity of the magnetic sensor.

BRIEF DESCRIPTION OF THE DRAWINGS

FIG. 4 is a table illustrating the characteristics of the magnetic sensor;

FIG. 9A is a perspective plan view;

FIG. 11A to FIG. 11C are schematic views illustrating another magnetic sensor according to the second embodiment;

DETAILED DESCRIPTION

Figures 1A, 1B:
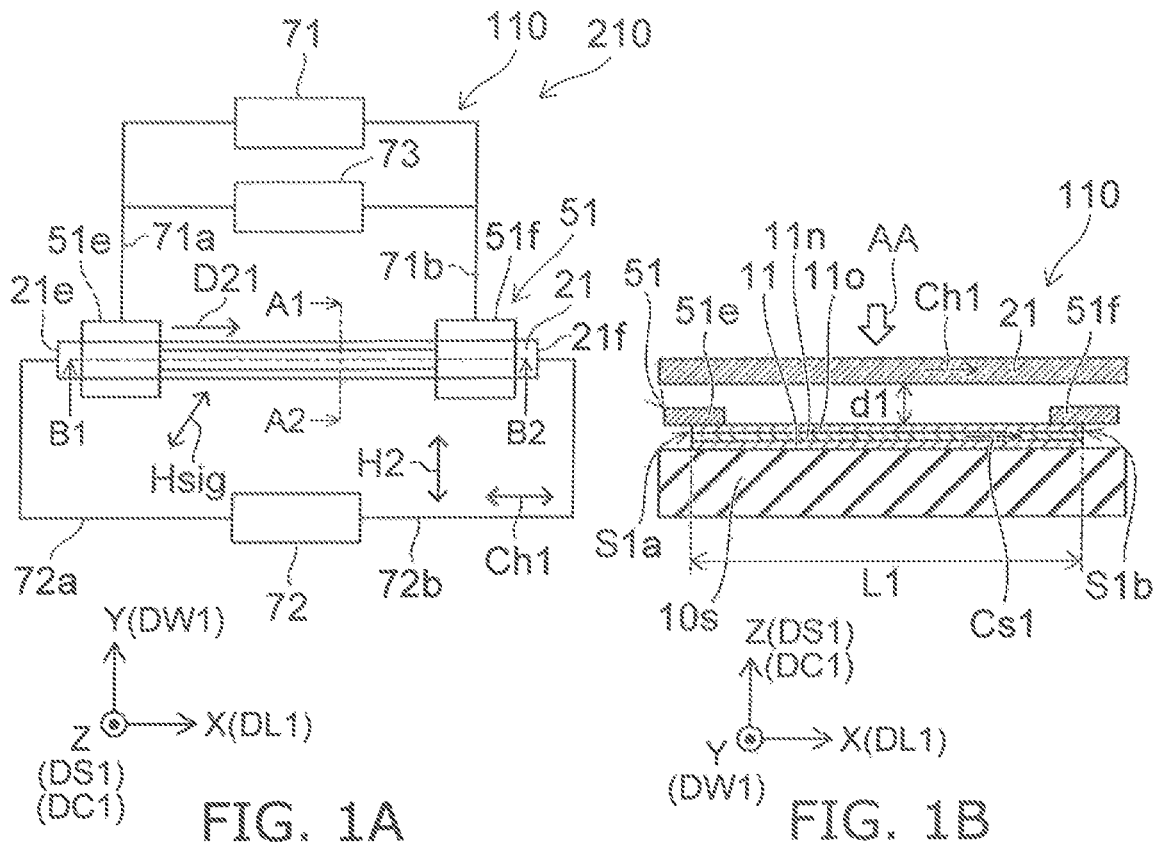
FIG. 1A to FIG. 1D are schematic views illustrating a magnetic sensor according to a first embodiment.

According to one embodiment, a magnetic sensor includes a first sensor element and a first interconnect. The first sensor element includes a first magnetic layer, a first opposing magnetic layer, and a first nonmagnetic layer provided between the first magnetic layer and the first opposing magnetic layer. A first magnetization of the first magnetic layer is aligned with a first length direction. A first stacking direction from the first magnetic layer toward the first opposing magnetic layer crosses the first length direction. At least a portion of the first interconnect extends along the first length direction. A first interconnect cross direction crosses the first length direction. The first interconnect cross direction is from the first sensor element toward the at least a portion of the first interconnect. A first electrical resistance of the first sensor element changes according to an alternating current flowing in the first interconnect and a sensed magnetic field applied to the first sensor element.

Various embodiments will be described hereinafter with reference to the accompanying drawings.

The drawings are schematic and conceptual; and the relationships between the thickness and width of portions, the proportions of sizes among portions, etc., are not necessarily the same as the actual values thereof. Further, the dimensions and proportions may be illustrated differently among drawings, even for identical portions.

In the specification and drawings, components similar to those described or illustrated in a drawing thereinabove are marked with like reference numerals, and a detailed description is omitted as appropriate.

First Embodiment

Figures 1C, 1D:
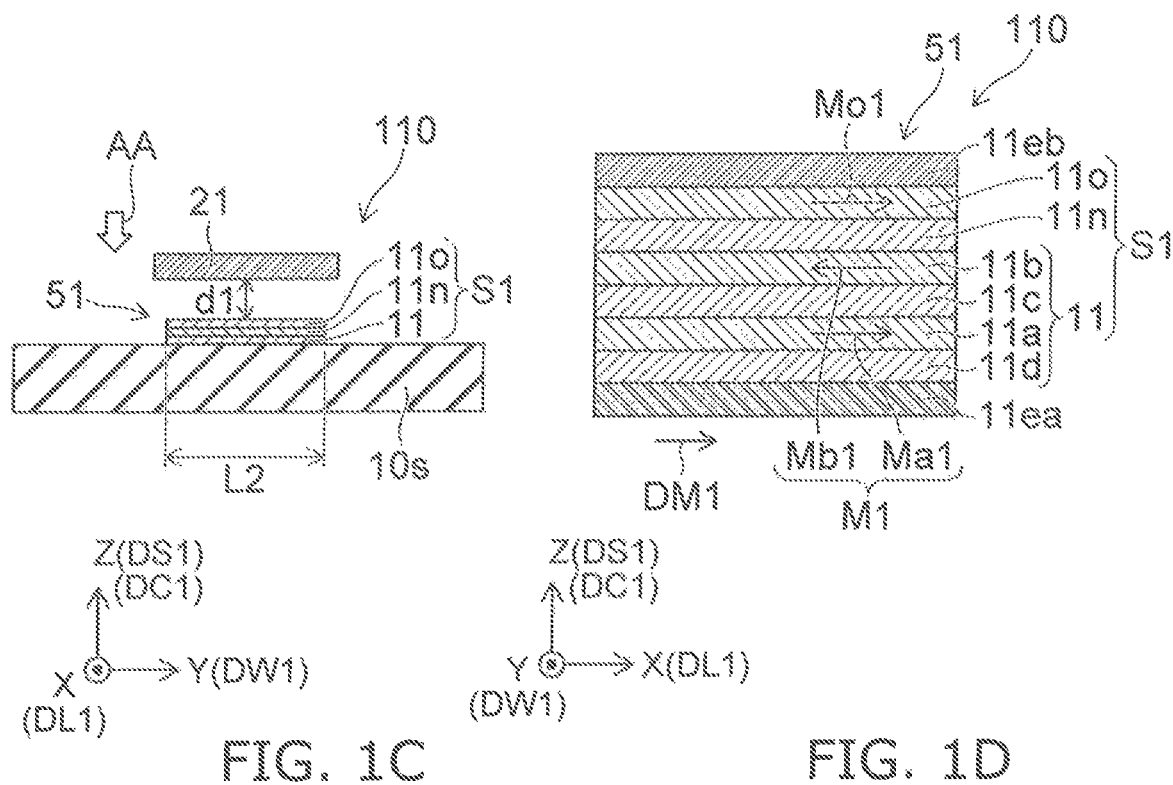

FIG. 1A to FIG. 1D are schematic views illustrating a magnetic sensor according to a first embodiment. FIG. 1A is a perspective plan view as viewed along arrow AA of FIG. 1B and FIG. 1C. FIG. 1B is a line B1-B2 cross-sectional view of FIG. 1A. FIG. 1C is a line A1-A2 cross-sectional view of FIG. 1A. FIG. 1D is a cross-sectional view of a portion of the magnetic sensor.

As shown in FIG. 1A, the magnetic sensor 110 according to the embodiment includes a first sensor element 51 and a first interconnect 21. In the example, the magnetic sensor 110 further includes a first circuit 71, a second circuit 72, and a third circuit 73. The magnetic sensor 110 and these circuits may be included in a magnetic sensor device 210.

As shown in FIG. 1D, the first sensor element 51 includes a first magnetic layer 11, a first opposing magnetic layer 11o, and a first nonmagnetic layer 11n. The first nonmagnetic layer 11n is provided between the first magnetic layer 11 and the first opposing magnetic layer 11o.

A first magnetization M1 of the first magnetic layer 11 is aligned with a first length direction DL1.

The first length direction DL1 is taken as an X-axis direction. One direction perpendicular to the X-axis direction is taken as a Y-axis direction. A direction perpendicular to the X-axis direction and the Y-axis direction is taken as a Z-axis direction.

A first stacking direction DS1 from the first magnetic layer 11 toward the first opposing magnetic layer 11o crosses the first length direction DL1. In the example, the first stacking direction DS1 is aligned with the Z-axis direction.

In the example, the first magnetic layer 11 is provided between a first element conductive layer 11ea and a second element conductive layer 11eb. The first opposing magnetic layer 11o is provided between the first magnetic layer 11 and the second element conductive layer 11eb. In the example, the first magnetic layer 11 includes a first film 11a, a second film 11b, a third film 11e, and a fourth film 11d. The second film 11b is positioned between the fourth film 11d and the first nonmagnetic layer 11n. The first film 11a is positioned between the fourth film 11d and the second film 11b. The third film 11e is positioned between the first film 11a and the second film 11b.

The first film 11a is, for example, a magnetic film. The first film 11a includes, for example, CoFe, etc. The second film 11b is a magnetic film. The second film 11b includes, for example, CoFe, etc. The third film 11c includes, for example, Ru. For example, the third film 11c generates antiferromagnetic coupling. The fourth film 11d is an anti ferromagnetic film. The fourth film 11d includes, for example, IrMn, etc. A magnetization Ma1 of the first film 11a is aligned with the first length direction DL1. A magnetization Mb1 of the second film 11b is aligned with the first length direction DL1. The orientation of the magnetization Ma1 is the reverse of the orientation of the magnetization Mb1. The first magnetization M1 of the first magnetic layer 11 is substantially fixed. The first magnetic layer 11 functions as, for example, a reference layer.

The length in the first length direction DL1 of the first magnetic layer 11 is taken as a first length L1 (referring to FIG. 1B). The length in a first width direction DW1 of the first magnetic layer 11 is taken as a second length L2 (referring to FIG. 1C). The first width direction DW1 crosses a plane (e.g., the X-Z plane) including the first stacking direction DS1 and the first length direction DL1. In the example, the first width direction DW1 is, for example, the Y-axis direction. The first length L1 is longer than the second length L2. For example, the first length L1 is not less than 1.5 times the second length L2. For example, shape anisotropy is provided in the first magnetic layer 11. For example, the first magnetization M1 of the first magnetic layer 11 is easier to stabilize.

The first magnetization M1 of the first magnetic layer 11 may be controlled by, for example, the direction of a magnetic field applied in the film deposition of a film included in the first magnetic layer 11. The first magnetization M1 of the first magnetic layer 11 may be controlled by, for example, the direction of a magnetic field applied in heat treatment after the film deposition of a film included in the first magnetic layer 11.

The first opposing magnetic layer 11o includes, for example, at least one selected from the group consisting of CoFe and NiFe. The orientation of a magnetization Mo1 of the first opposing magnetic layer 11o changes according to the magnetic field applied to the first opposing magnetic layer 11o, etc. The first opposing magnetic layer 11o is, for example, a free layer.

The first nonmagnetic layer 11n includes, for example, Cu, etc.

In the example, the planar configurations (the configurations in a plane aligned with the X-Y plane) of the first opposing magnetic layer 11o and the first nonmagnetic layer 11n are the same as the planar configuration of the first magnetic layer 11.

The first element conductive layer 11ea includes, for example, at least one selected from the group consisting of Ta, Cu, and Ru. The first element conductive layer 11ea may include, for example, NiFeCr. The first element conductive layer 11ea may function as, for example, a buffer layer.

The second element conductive layer 11eb includes, for example, at least one selected from the group consisting of Ru and Ta. The second element conductive layer 11eb may function as, for example, a capping layer.

The first magnetic layer 11, the first opposing magnetic layer 11o, and the first nonmagnetic layer 11n are included in a first stacked portion S1. The first element conductive layer 11ea and the second element conductive layer 11eb may be included in the first stacked portion S1. The first element conductive layer 11ea and the second element conductive layer 11eb are not illustrated in FIG. 1B and FIG. 1C. As shown in FIG. 1B, the first stacked portion S1 includes one end portion S1a and another end portion S1b. The direction from the one end portion S1a toward the other end portion S1b is aligned with the first length direction DL1. In the example, the first stacked portion S1 is, for example, a GMR (Giant Magneto Resistive effect) element.

As shown in FIG. 1A and FIG. 1B, at least a portion of the first interconnect 21 extends along the first length direction DL1. As shown in FIG. 1B, the direction (a first interconnect cross direction DC1) from the first sensor element 51 toward the at least a portion of the first interconnect 21 recited above crosses the first length direction DL1. In the example, the first interconnect cross direction DC1 is the Z-axis direction. In the example, the first interconnect cross direction DC1 is aligned with the first stacking direction DS1.

As shown in FIG. 1B and FIG. 1C, a substrate 10s is provided in the example. The first sensor element 51 is positioned between the substrate 10s and the first interconnect 21. The substrate 10s is not illustrated in FIG. 1A.

As described below, a first electrical resistance of the first sensor element 51 changes according to an alternate current flowing in the first interconnect 21 and a sensed magnetic field (a signal magnetic field Hsig applied from the outside) applied to the first sensor element 51.

For example, as shown in FIG. 1B, a first sensor one-end interconnect 51e is electrically connected to the one end portion S1a of the first stacked portion S1. On the other hand, a first sensor other-end interconnect 51f is electrically connected to the other end portion S1b of the first stacked portion S1. The change of the first electrical resistance of the first sensor element 51 corresponds to the change of the electrical resistance between the one end portion S1a and the other end portion S1b. The change of the first electrical resistance corresponds to the change of the electrical resistance between the first sensor one-end interconnect 51e and the first sensor other-end interconnect 51f. The first sensor one-end interconnect 51e and the first sensor other-end interconnect 51f may be electrode terminals.

The first circuit 71 is electrically connected to the first sensor element 51. In the example, the first circuit 71 is electrically connected to the first sensor element 51 via an interconnect 71a and an interconnect 71b. The first circuit 71 supplies a first direct current Cs1 to the first sensor element 51 (referring to FIG. 1B).

In the example, the first current Cs1 flows through the first stacked portion S1 along the first length direction DL1.

The third circuit 73 senses the change of the first electrical resistance of the first sensor element 51. For example, the third circuit 73 is connected in parallel with the first circuit 71. For example, the third circuit 73 is electrically connected to the first stacked portion S1 via the interconnect 71a and the interconnect 71b. The third circuit 73 senses at least one of a voltage, a current, or a resistance corresponding to the first electrical resistance of the first sensor element 51.

As shown in FIG. 1A, the second circuit 72 is electrically connected to the first interconnect 21. In the example, the second circuit 72 is electrically connected to one end 21e of the first interconnect 21 by an interconnect 72a. The second circuit 72 is electrically connected to another end 21f of the first interconnect 21 by an interconnect 72b. The second circuit 72 supplies a second current Ch1 to the first interconnect 21. As described below, the second current Ch1 is, for example, an alternating current signal. A magnetic field H2 is generated by the second current Ch1 flowing through the first interconnect 21. The magnetic field H2 is applied to the first sensor element 51.

In the case where a distance d1 between the first sensor element 51 and the first interconnect 21 (referring to FIG. 1B and FIG. 1C) is small, for example, the magnetic field H2 that is generated by the current flowing in the first interconnect 21 is applied effectively to the first sensor element 51. In the case where the distance d1 is excessively small, the current (the direct current) that is supplied to the first sensor element 51 may be affected by effects of capacitive coupling when the alternating current signal is supplied to the first interconnect 21. For example, the distance d1 is not less than 0.1 μm and not more than 120 μm. By setting the distance d1 to be 120 μm or less, the magnetic field H2 is applied effectively to the first sensor element 51. The effects of the capacitive coupling are suppressed when the distance d1 is 0.1 μm or more. It is more favorable for the distance d1 to be, for example, 0.5 μm or more. It is more favorable for the distance d1 to be, for example, 1 μm or more. It is more favorable for the distance d1 to be 30 μm or less. It is more favorable for the distance d1 to be 15 μm or less.

For example, the width (the second length L2) of the first magnetic layer 11 is 1 μm; and the distance d1 between the first interconnect 21 and the first sensor element 51 is set to 1 μm. The current that flows in the first interconnect 21 is set to 1 mA. In such a case, the magnetic field H2 that is applied to the first sensor element 51 is 1000 A/m (i.e., 12.5 Oe (oersteds)). The direction of the magnetic field H2 is aligned with the Y-axis direction. As described below, the sensed magnetic field is sensed by using an alternating current magnetic field H2 having a Y-axis direction component.

For example, in the case where the current (the second current Ch1) that flows in the first interconnect 21 is zero, the orientation of the magnetization Mo1 of the first opposing magnetic layer 11o is aligned with the X-axis direction. In the case where the current (the second current Ch1) that flows in the first interconnect 21 is nonzero, for example, the orientation of the magnetization Mo1 of the first opposing magnetic layer 11o changes due to the magnetic field H2 generated by the current. For example, the orientation of the magnetization Mo1 changes toward the Y-axis direction. As a result, the angle changes between the first magnetization H1 of the first magnetic layer 11 and the magnetization Mo1 of the first opposing magnetic layer 11o. Thereby, the electrical resistance (the first electrical resistance) changes between the first magnetic layer 11 and the first opposing magnetic layer 11o.

Further, the orientation of the magnetization Mo1 of the first opposing magnetic layer 11o changes when the sensed magnetic field (the signal magnetic field Hsig) to be sensed is applied to the first sensor element 51. As a result, the angle changes between the first magnetization M1 of the first magnetic layer 11 and the magnetization Mo1 of the first opposing magnetic layer 11o. Thereby, the electrical resistance (the first electrical resistance) between the first magnetic layer 11 and the first opposing magnetic layer 11o changes.

Thus, in the embodiment, the first electrical resistance of the first sensor element 51 changes according to the second current Ch1 flowing in the first interconnect 21 and the sensed magnetic field (the signal magnetic field Hsig) applied to the first sensor element 51.

High-sensitivity is obtained in such a magnetic sensor 110. Examples of the characteristics of the magnetic sensor 110 will now be described.

Figure 2A:
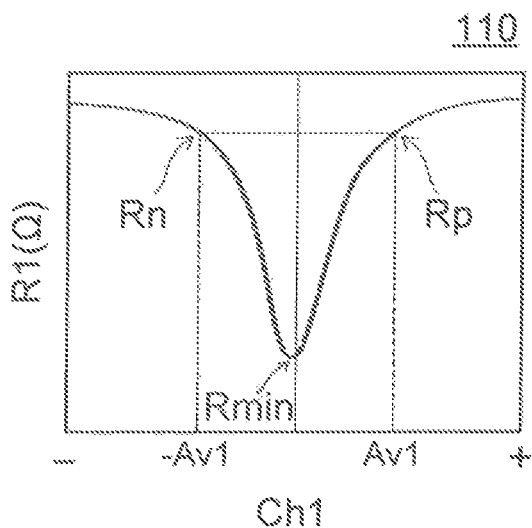
FIG. 2A and FIG. 2B are graphs illustrating characteristics of the magnetic sensor according to the first embodiment.
Figure 2B:
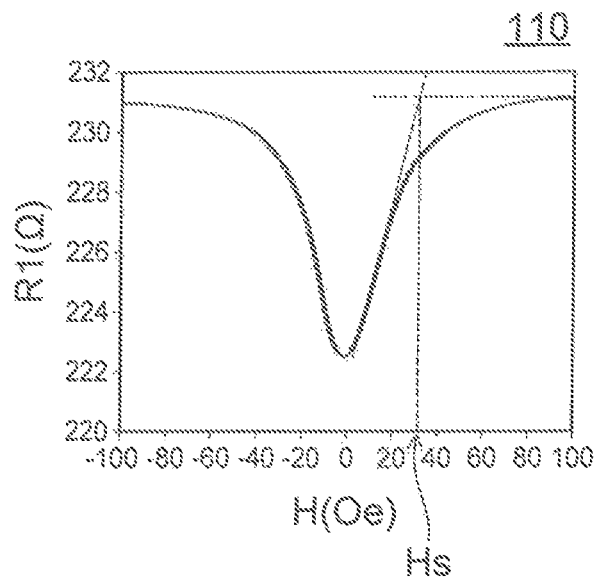

FIG. 2A and FIG. 2B are graphs illustrating characteristics of the magnetic sensor according to the first embodiment.

These figures illustrate simulation results of the characteristics of the magnetic sensor 110. In the example, the width (the second length L2) of the first magnetic layer 11 is 10 μm; and the length (the first length L1) of the first magnetic layer 11 is 250 μm. The distance d1 between the first interconnect 21 and the first sensor element 51 is 0.5 μm. The horizontal axis of FIG. 2A is the second current Ch1 flowing in the first interconnect 21. The horizontal axis of FIG. 2B is a magnetic field H (Oe) (corresponding to the magnetic field H2) generated by the second current Ch1. In these figures, the vertical axis is a first electrical resistance R1.

As shown in FIG. 2A, the first electrical resistance R1 is substantially symmetric with respect to the positive and negative second current Ch1.

For example, the first electrical resistance R1 increases when the current (the second current Ch1) flowing in the first interconnect 21 has a positive polarity and the absolute value of the current increases. The first electrical resistance R1 increases when the current (the second current Ch1) flowing in the first interconnect 21 has a negative polarity and the absolute value of the current increases. The first electrical resistance R1 has substantially a minimum when the second current Ch1 is 0.

For example, the difference is small between the first electrical resistance R1 (Rp) when the second current Ch1 having the positive polarity is a first absolute value Av1 and the first electrical resistance R1 (Rn) when the second current Ch1 having the negative polarity is the first absolute value Av1. For example, the ratio (|Rp−Rn|/Rp), which is the absolute value of the difference between the first electrical resistance R1 when the second current Ch1 having the positive polarity is the first absolute value Av1 and the first electrical resistance R1 when the second current Ch1 having the negative polarity is the first absolute value Av1 to the first electrical resistance R1 when the second current Ch1 having the positive polarity is the first absolute value Av1, is about 0.03 or less. The ratio may be 0.01 or less.

For example, when the current (the second current Ch1) does not flow in the first interconnect 21, the first electrical resistance R1 of the first sensor element 51 has substantially a minimum. The value of the minimum of the first electrical resistance R1 obtained when changing the second current Ch1 is taken as a minimum value Rmin. For example, when the second current Ch1 is 0, the first electrical resistance R1 is more than 1 times and not more than 1.002 times the minimum value Rmin. For example, when the second current Ch1 is 0, the first electrical resistance R1 may be more than 1 times and not more than 1.001 times the minimum value Rmin.

As shown in FIG. 2B, the first electrical resistance R1 is substantially symmetric with respect to the positive and negative magnetic field H. Thus, in the magnetic sensor 110, a resistance-magnetic field characteristic (R-H characteristic) that is an even function is obtained in which the increased resistance is symmetric with respect to the positive and negative magnetic field. The magnetic field (a saturation magnetic field Hs) at which the increase of the first electrical resistance R1 is saturated is about 30 Oe. Hysteresis Hc is about 0.15 Oe. The hysteresis Hc is very small. The noise can be small because the hysteresis Hc is small. According to the embodiment, a magnetic sensor can be provided in which the sensitivity can be increased.

Figure 3A:
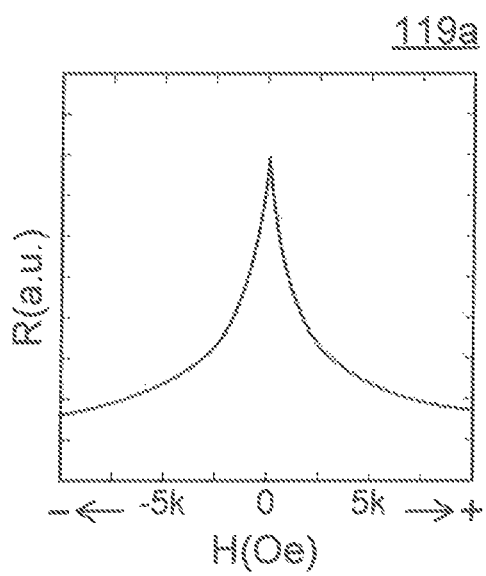
FIG. 3A and FIG. 3B are graphs illustrating characteristics of magnetic sensors of a reference example.
Figure 3B:
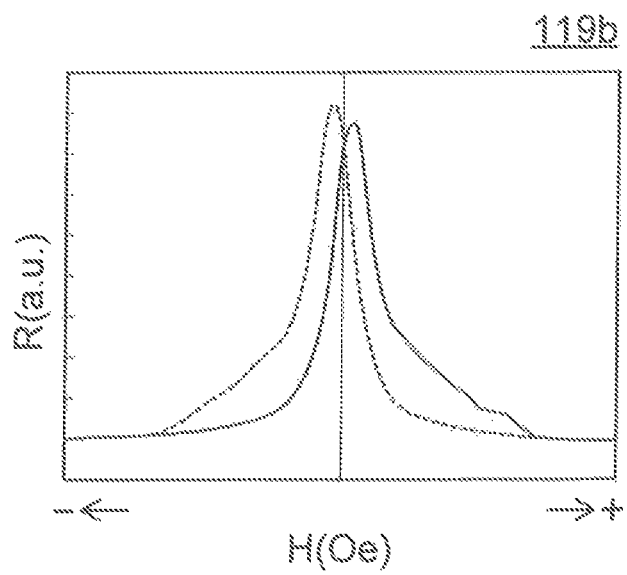

FIG. 3A and FIG. 3B are graphs illustrating characteristics of magnetic sensors of a reference example. FIG. 3A shows an example of the R-H characteristic of a magnetic sensor 119a of the reference example. In a magnetic sensor 119b, a granular TMR configuration is used. An R-H characteristic that is an even function is obtained in the reference example. However, the saturation magnetic field Hs is about 3 kOe and is extremely large. The change amount of a resistance R due to the magnetic field H is small.

FIG. 3B shows an example of the R-H characteristic of a magnetic sensor 119b of the reference example. In the magnetic sensor 119b, a free layer/nonmagnetic intermediate layer/free layer configuration is used. An R-H characteristic that is an even function is obtained in the reference example. However, the hysteresis Hc is large. For example, the hysteresis Hc is about 15 Oe when the saturation magnetic field Hs is about 30 Oe.

FIG. 4 is a table illustrating the characteristics of the magnetic sensor.

FIG. 4 shows the hysteresis Hc and the saturation magnetic field Hs for stacked bodies having various configurations. The first stacked portion S1 of the samples includes the first magnetic layer 11, the first opposing magnetic layer 11o, and the first nonmagnetic layer 11n. The length (the first length L1) of the first magnetic layer 1 and the width (the second length L2) of the first magnetic layer 11 are modified. In the example, the first interconnect 21 is not provided in the samples. An external magnetic field is applied to the samples; and the R-H characteristic at that time is measured. An orientation DM1 of the first magnetization M1 of the first magnetic layer 11 is modified for the various configurations (referring to FIGS. 1A to 1D). Also, a direction D21 in which the first interconnect 21 extends is modified (referring to FIG. 1A). The direction D21 corresponds to the direction of the second current Ch1 flowing through the first interconnect 21. An external magnetic field that is in a direction along the film surface and orthogonal to the direction D21 is applied to the first stacked portion S1. The values of the hysteresis Hc and the saturation magnetic field Hs shown in FIG. 4 are determined from the R-H characteristic when an alternating-current magnetic field of 25 Oe is applied.

In configurations SP11 to SP15, the hysteresis Hc is 0.25 Oe or less. In the configurations SP21 to SP24, SP31 to SP34, and SP41 to SP44, the hysteresis Hc is 1 Oe or more and is large.

Thus, a small hysteresis Hc is obtained when the orientation DM1 of the first magnetization M1 of the first magnetic layer 11 and the direction D21 in which the first interconnect 21 extends are aligned with the X-axis direction (the first length direction DL1). In such a configuration, the noise can be small; and high sensing sensitivity is obtained.

For example, a Cu film having a thickness of not less than 2.5 nm and not more than 3.5 nm is used as the first nonmagnetic layer 11n. In such a first nonmagnetic layer 11n, the negative effects on the saturation magnetic field Hs are small. By using such a first nonmagnetic layer 11n, for example, a coupling magnetic field can be induced between the first opposing magnetic layer 11o and the first magnetic layer 11. Thereby, for example, a small hysteresis Hc can be obtained while the first opposing magnetic layer 11o is a single magnetic domain. For example, there is a configuration in which a hard magnetic film is provided at the vicinity of the first opposing magnetic layer 11o to obtain a small hysteresis Hc using the first opposing magnetic layer 11o that is the single magnetic domain. In such a case, the processes are complex. By using a first nonmagnetic layer 11n such as that recited above, a small hysteresis Hc is obtained without using complex processes.

An operation example of the magnetic sensor 110 will now be described. In the following example, the second current Ch1 that is alternating current flows in the first interconnect 21. In other words, the second circuit 72 supplies the second current Ch1 which is alternating current to the first interconnect 21. The second current Ch1 has an alternating current component. An alternating-current magnetic field Hac is generated by the alternating current component. The direction of the alternating-current magnetic field Hac is aligned with the Y-axis direction. The alternating-current magnetic field Hac and the sensed magnetic field (the signal magnetic field Hsig) to be sensed are applied to the first sensor element 51.

Figure 5A:
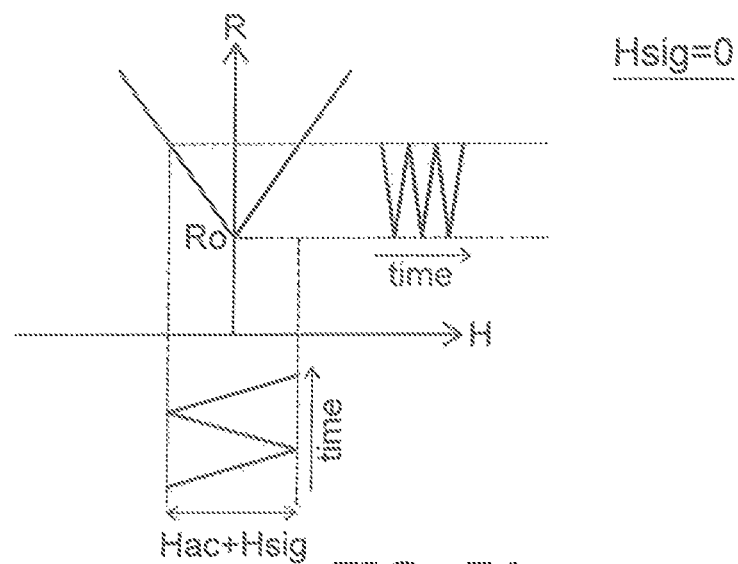
FIG. 5A to FIG. 5C are graphs illustrating characteristics of the magnetic sensor according to the first embodiment.
Figure 5B:
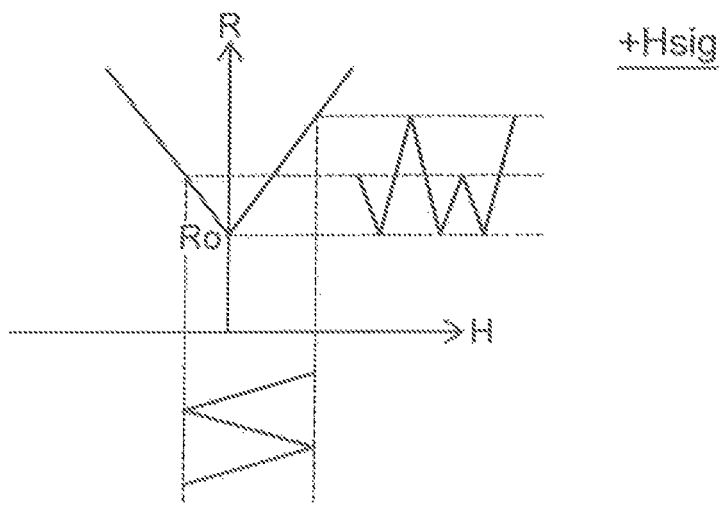
Figure 5C:
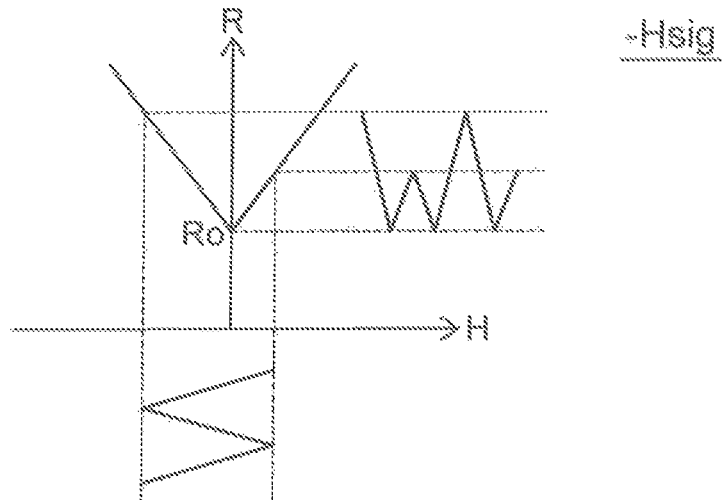

FIG. 5A to FIG. 5C are graphs illustrating characteristics of the magnetic sensor according to the first embodiment.

FIG. 5A shows characteristics when the signal magnetic field Hsig is 0. FIG. 5B shows characteristics when the signal magnetic field Hsig is positive. FIG. 5C shows characteristics when the signal magnetic field Hsig is negative. These figures show the relationship between the magnetic field H and the resistance R (corresponding to the first electrical resistance R1).

As shown in FIG. 5A, when the signal magnetic field Hsig is 0, the resistance R has a characteristic that is symmetric with respect to the positive and negative magnetic field H. When the alternating current is zero, the resistance R is a low resistance Ro. The magnetization of the first opposing magnetic layer 11o (e.g., a free layer) rotates substantially identically to the positive and negative magnetic field H. Therefore, symmetric increased resistance characteristics are obtained. The fluctuation of the resistance R with respect to the alternating current (the alternating-current magnetic field Hac) has the same value between the positive and negative polarities. The period of the change of the resistance R is 2 times the period of the alternating-current magnetic field Hac. The change of the resistance R substantially does not include the frequency component of the alternating-current magnetic field Hac.

As shown in FIG. 5B, the characteristic of the resistance R shifts to the positive magnetic field H side when a positive signal magnetic field Hsig is applied. The resistance R becomes large for the alternating-current magnetic field Hac on the positive side. The resistance R becomes small for the alternating-current magnetic field Hac on the negative side.

As shown in FIG. 5C, the characteristic of the resistance R shifts to the negative magnetic field H side when a negative signal magnetic field Hsig is applied. The resistance R becomes small for the alternating-current magnetic field Hac on the positive side. The resistance R becomes large for the alternating-current magnetic field Hac on the negative side.

Resistances R having mutually-different fluctuation occur for the positive and negative alternating-current magnetic field Hac when a signal magnetic field Hsig is applied. The period of the fluctuation of the resistance R with respect to the positive and negative alternating-current magnetic field Hac is the same as the period of the alternating-current magnetic field Hac (the period of the alternating current component of the second current Ch1). An output voltage that has an alternating current frequency component corresponding to the signal magnetic field Hsig is generated.

The characteristics recited above are obtained in the case where the signal magnetic field Hsig does not change temporally. The case where the signal magnetic field Hsig changes temporally is as follows. The frequency of the signal magnetic field Hsig is taken as a signal frequency fsig. The frequency of the alternating-current magnetic field Hac is taken as an alternating current frequency fac. In such a case, an output that corresponds to the signal magnetic field Hsig at frequencies of fac±fsig is generated.

In the case where the signal magnetic field Hsig changes temporally, the signal frequency fsig is, for example, 1 kHz or less. On the other hand, the alternating current frequency fac is sufficiently higher than the signal frequency fsig. For example, the alternating current frequency fac is not less than 10 times the signal frequency fsig.

For example, there is an application in which the magnetic field generated from a living body is sensed using the magnetic sensor 110. In the case where such a biological magnetic field (e.g., neuromagnetism, cardiomagnetism, a neuron, or the like) is sensed, the signal frequency fsig is 1 kHz or less. In such a case, the alternating current frequency fac is, for example, 100 kHz or more.

In the magnetic sensor 110 according to the embodiment, the sensed magnetic field (the signal magnetic field Hsig) that is to be sensed can be sensed with high sensitivity using such characteristics. An example of the sensing will now be described.

FIG. 6A to FIG. 6D are schematic views illustrating sense circuits of magnetic sensors according to the first embodiment.

Figure 6A:
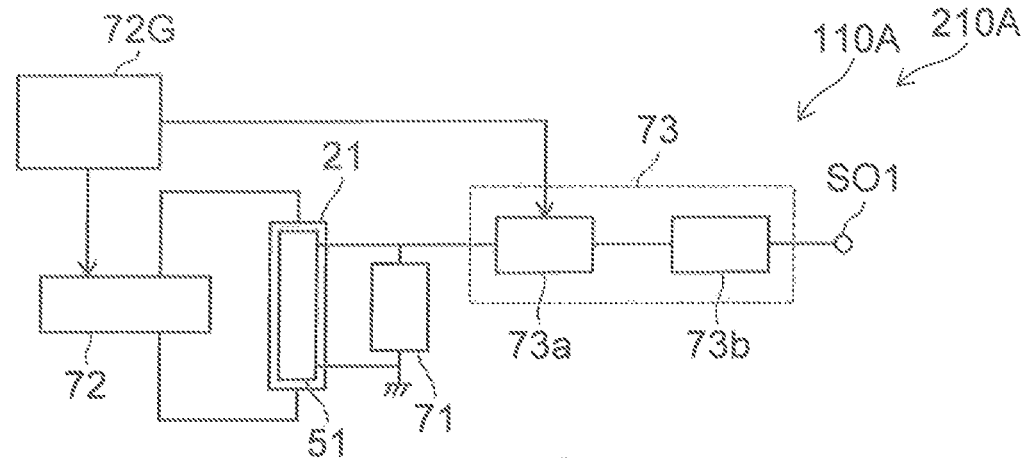
FIG. 6A to FIG. 6D are schematic views illustrating sense circuits of magnetic sensors according to the first embodiment.

A frequency generator 72G is provided in a magnetic sensor 110A and a magnetic sensor device 210A shown in FIG. 6A. The frequency generator 72G generates a signal having the alternating current frequency fac (a first frequency). This signal is supplied to the second circuit 72. The second circuit 72 supplies, to the first interconnect 21, the second current Ch1 having the alternating current frequency fac (the first frequency).

On the other hand, a direct current (the first current Cs1) is supplied by the first circuit 71 to the first sensor element 51.

In the example, the third circuit 73 includes a lock-in amplifier 73a. The signal that is generated by the frequency generator 72G and has the alternating current frequency fac (the first frequency) is input to the lock-in amplifier 73a. For example, the lock-in amplifier 73a senses an alternating current signal having a frequency in a range including the first frequency (the alternating current frequency fac). In the example, the output of the lock-in amplifier 73a is output as an output signal SO1 via a low-pass filter 73b. Thereby, the output signal SO1 is a signal corresponding to the signal magnetic field Hsig.

Figure 6B:
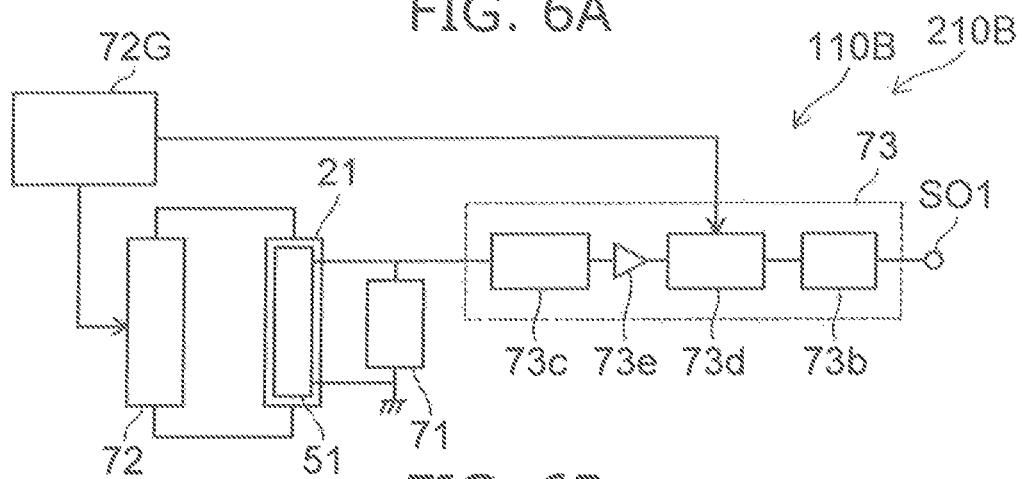

A band-pass filter 73c and a PSD (phase sensitive detector) circuit 73d are provided in a magnetic sensor 110B and a magnetic sensor device 210B shown in FIG. 6B. A signal that corresponds to the first electrical resistance R1 is input to the band-pass filter 73c. For example, the band-pass filter 73c attenuates signals of frequencies not less than 2 times the first frequency (the alternating current frequency fac). The output of the band-pass filter 73c is input to the PSD circuit 73d. In the example, the output of the band-pass filter 73c is input to an amplifier 73e; and the output of the amplifier 73e is input to the PSD circuit 73d. The signal that is generated by the frequency generator 72G and has the alternating current frequency fac (the first frequency) is input to the PSD circuit 73d.

For example, the highest frequency of the signal magnetic field Hsig is taken as a maximum frequency fsigm. In such a case, for example, the band-pass filter 73c transmits frequencies in the range of fac±fsigm. Also, the band-pass filter 73c attenuates (e.g., cuts) frequency components that are 2 times the alternating current frequency fac or more.

In such a case as well, the output of the PSD circuit 73d is output as the output signal SO1 via the low-pass filter 73b. Thereby, the output signal SO1 is a signal corresponding to the signal magnetic field Hsig.

Figures 6C, 6D:
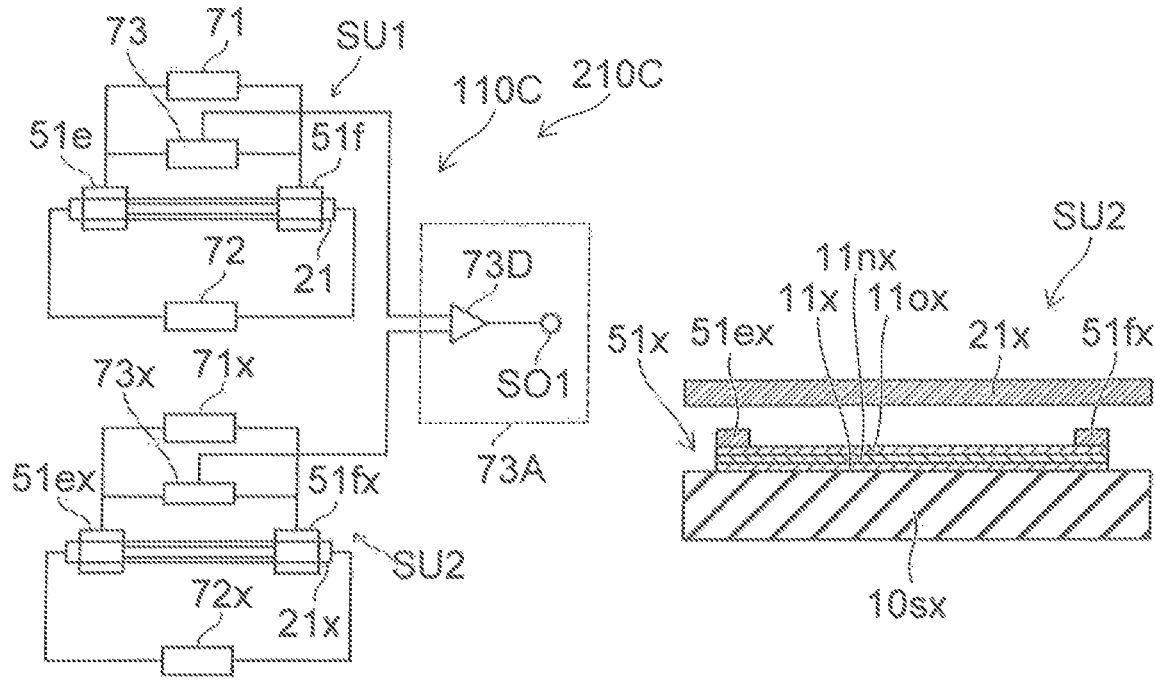

A first sensor portion SU1 and a second sensor portion SU2 are provided in a magnetic sensor 110C and a magnetic sensor device 210C shown in FIG. 6C. The first sensor portion SU1 includes the first sensor element 51, the first interconnect 21, the first circuit 71, the second circuit 72, and the third circuit 73 recited above. The second sensor portion SU2 includes a stacked body 51X, an interconnect 21X, another first circuit 71X, another second circuit 72X, and another third circuit 73X. The first circuit 71 and the second circuit 72 may be shared by the first sensor portion SU1 and the second sensor portion SU2. In such a case, the other first circuit 71X and the other second circuit 72X are omitted. Hereinbelow, the case is described where the other first circuit 71X and the other second circuit 72X are provided.

In the second sensor portion SU2 as shown in FIG. 6D, the stacked body 51X includes a nonmagnetic layer 11nX and two magnetic layers (a magnetic layer 11X and a magnetic layer 11oX). The nonmagnetic layer 11nX is provided between the two magnetic layers 11X and 11oX. A first stacked body one-end interconnect 51eX is electrically connected to one end of the stacked body 51X. A first stacked body other-end interconnect 51fX is electrically connected to the other end of the stacked body 51X.

The configuration of the stacked body 51X is similar to, for example, the configuration of the first sensor element 51. The configuration of the interconnect 21X is similar to, for example, the configuration of the first interconnect 21. The configuration of the other first circuit 71X is similar to, for example, the configuration of the first circuit 71. The configuration of the other second circuit 72X is similar to, for example, the configuration of the second circuit 72. The configuration of the other third circuit 73X is similar to, for example, the configuration of the third circuit 73. For example, the characteristics of the second sensor portion SU2 are substantially the same as the characteristics of the first sensor portion SU1.

The spatial position of the second sensor portion SU2 is different from the spatial position of the first sensor portion SU1. For example, the strength of the sensed magnetic field (the signal magnetic field Hsig) applied to the second sensor portion SU2 (the stacked body 51X) is smaller than the strength of the sensed magnetic field applied to the first sensor portion SU1 (the first sensor element 51).

For example, a current that includes the same signal as the signal supplied to the first sensor element 51 from the first circuit 71 is supplied to the stacked body 51X from the other first circuit 71X. For example, a current that includes the same signal as the signal supplied to the first interconnect 21 from the second circuit 72 is supplied to the interconnect 21X from the other second circuit 72X.

The signal obtained from the second sensor portion SU2 (e.g., the output of the other third circuit 73X) and the signal obtained from the first sensor portion SU1 are supplied to a sense circuit 73A. The sense circuit 73A outputs a signal corresponding to the difference of these two signals. In the example, the sense circuit 73A includes a differential amplifier 73D. The signal obtained from the second sensor portion SU2 and the signal obtained from the first sensor portion SU1 are input to the differential amplifier 73D. The differential amplifier 73D outputs a signal corresponding to the difference of these signals. The sense circuit 73A may be considered to be a portion of the third circuit 73 of the first sensor portion SU1.

By using such a configuration, for example, the sensed magnetic field (the signal magnetic field Hsig) that is to be sensed can be sensed with high sensitivity.

For example, there are cases where noise is generated by an external magnetic field that is different from the signal magnetic field Hsig. The effects of such noise can be reduced by a configuration including the stacked body 51X, the interconnect 21X, and the differential amplifier 73D recited above.

The external magnetic field that is the noise source can be considered to be uniform inside a space having a size of not less than 1 mm and not more than 10 cm. The distance between the second sensor portion SU2 and the first sensor portion SU1 is, for example, not less than 1 mm and not more than 10 cm. Thereby, the external magnetic field that is the noise source can be attenuated effectively.

For example, there are also cases where noise is generated by a static external magnetic field such as geomagnetic field. For example, a current (a compensation current) that has a component that attenuates the external magnetic field may be supplied to the first interconnect 21. For example, the second current Ch1 may include an alternating current component and a compensation component. Thereby, the effects of the noise due to the external magnetic field can be reduced. The effects of geomagnetic field can be compensated by direct current.

In the embodiment, the noise can be reduced. Thereby, high sensitivity is obtained practically. For example, a micro signal magnetic field Hsig can be sensed with low noise and high sensitivity. In the embodiment, for example, the distortion of the signal magnetic field Hsig is small; and a R-H characteristic that has a small hysteresis Hc and is an even function is obtained. In the embodiment, a hysteresis Hc that is smaller than the hysteresis Hc of a conventional linear-response R-H characteristic is obtained.

Several examples of the first sensor element 51 will now be described.

Figure 7A:
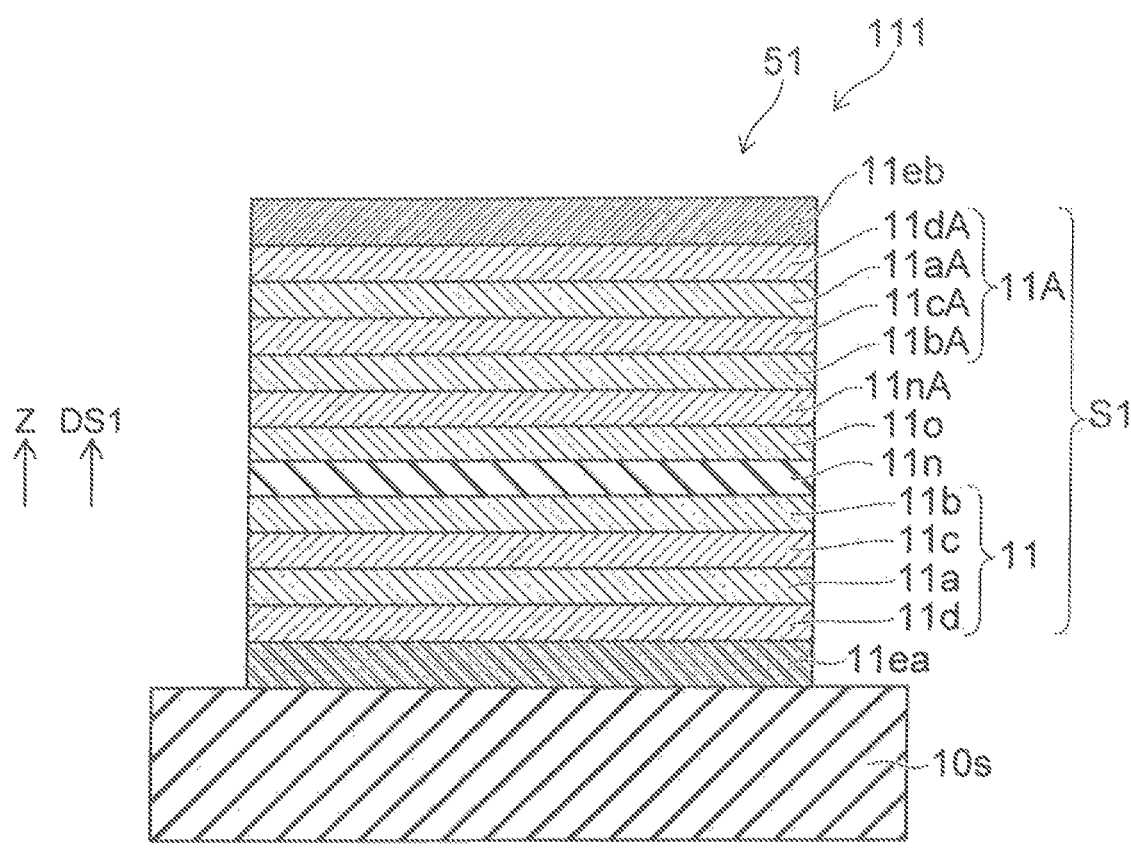
FIG. 7A and FIG. 7B are schematic cross-sectional views illustrating other magnetic sensors according to the first embodiment.
Figure 7B:
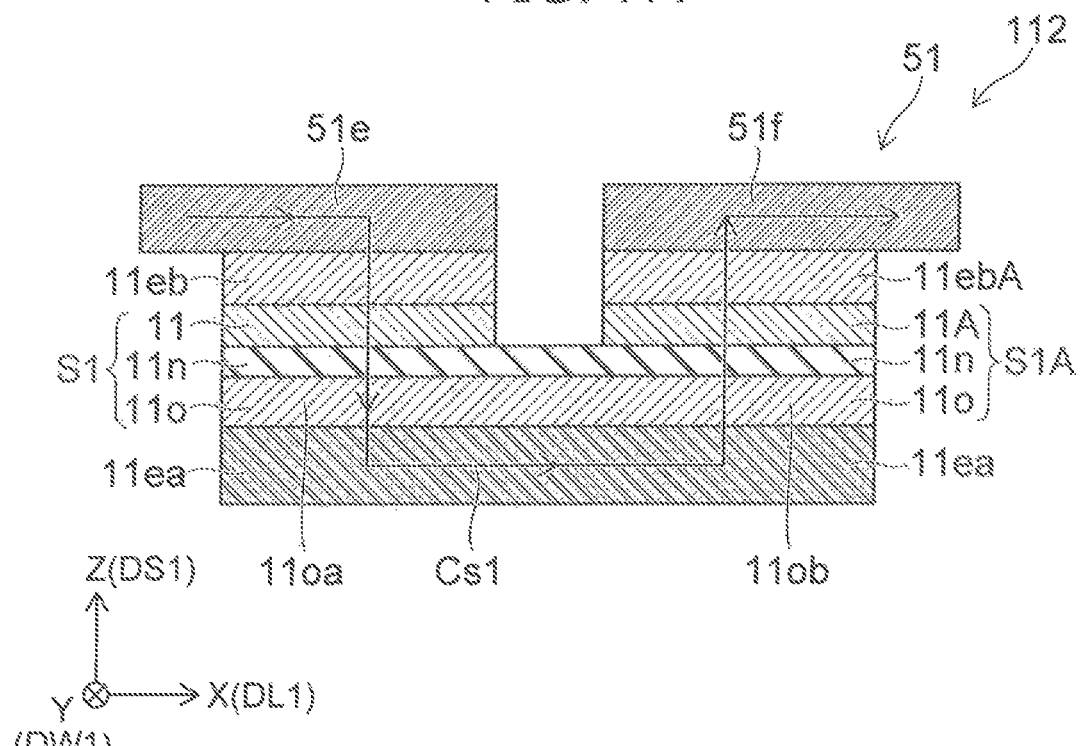

FIG. 7A and FIG. 7B are schematic cross-sectional views illustrating other magnetic sensors according to the first embodiment.

These drawings show other examples of the first sensor element 51.

In a magnetic sensor 111 as shown in FIG. 7A, the first sensor element 51 further includes another first magnetic layer 11A and another first nonmagnetic layer 11nA in addition to the first magnetic layer 11, the first opposing magnetic layer 11o, and the first nonmagnetic layer 11n. The configurations of the first magnetic layer 11, the first opposing magnetic layer 11o, and the first nonmagnetic layer 11n are similar to the respective configurations described above.

The first opposing magnetic layer 11o is positioned between the first magnetic layer 11 and the other first magnetic layer 11A in the first stacking direction DS1 (e.g., the Z-axis direction). The other first nonmagnetic layer 11nA is positioned between the other first magnetic layer 11A and the first opposing magnetic layer 11o in the first stacking direction DS1.

In the example, the first magnetic layer 11 and the other first magnetic layer 11A are provided between the first element conductive layer 11ea and the second element conductive layer 11eb.

In the example, the other first magnetic layer 11A includes another first film 11aA, another second film 11bA, another third film 11cA, and another fourth film 11dA. The other second film 11bA is positioned between the other fourth film 11dA and the other first nonmagnetic layer 11nA. The other first film 11aA is positioned between the other fourth film 11dA and the other second film 11bA. The other third film 11cA is positioned between the other first film 11aA and the other second film 11bA.

The configurations and materials of the first film 11a, the second film 11b, the third film 11e, and the fourth film 11d are applied respectively to the other first film 11aA, the other second film 11bA, the other third film 11cA, and the other fourth film 11dA.

In the magnetic sensor 111, the position of the first opposing magnetic layer 11o (e.g., the free layer) in the first sensor element 51 is positioned at substantially the central portion of the first sensor element 51. Thereby, for example, the magnetic field that is caused by a self-current flowing through the first sensor element 51 (in the first length direction DL1 in X-Y plane) can be substantially zero. Thereby, an R-H characteristic showing even function without distortion by the self-current is obtained. The resistance change ratio of the magnetic sensor 111 can be higher than the resistance change ratio of the magnetic sensor 110 illustrated in FIG. 1B. For example, the resistance change ratio of the magnetic sensor 111 is about 1.5 times the resistance change ratio of the magnetic sensor 110.

In the example of the magnetic sensor 111, the first nonmagnetic layer 11n includes, for example, MgO. The first nonmagnetic layer 11n includes, for example, an insulative material.

In the magnetic sensor 111, the first element conductive layer 11eb is electrically connected to the first sensor one-end interconnect 51e. The first sensor one-end interconnect 51e is connected to the first circuit 71 via the interconnect 71a. The second element conductive layer 11ebA is electrically connected to the first sensor other-end interconnect 51f. The first sensor other-end interconnect 51f is connected to the first circuit 71 via the interconnect 71b. The first current Cs1 flows through the first stacked portion S1 along the first stacking direction DS1 (the Z-axis direction).

In a magnetic sensor 112 as shown in FIG. 7B, the first sensor element 51 further includes the other first magnetic layer 11A in addition to the first magnetic layer 1, the first opposing magnetic layer 11o, and the first nonmagnetic layer 11n.

In the example, the first opposing magnetic layer 11o includes a first partial region 11oa and a second partial region 11ob. A portion of the first nonmagnetic layer 11n is positioned between the first magnetic layer 11 and the first partial region 11ea. Another portion of the first nonmagnetic layer 11n is positioned between the other first magnetic layer 11A and the second partial region 11ob.

In the example, the first partial region 11oa is provided between the first sensor one-end interconnect 51e and a portion of the first element conductive layer 11ea. The second element conductive layer, 11eb is provided between the first sensor one-end interconnect 51e and the first partial region 11oa. The first magnetic layer 11 and a portion of the first nonmagnetic layer 11n are provided between the first partial region 11oa and the second element conductive layer 11eb. The first partial region 11oa, the first magnetic layer 11, and the portion of the first nonmagnetic layer 11n are included in the first stacked portion S1.

The second partial region 11ob is provided between the first sensor other-end interconnect 51f and another portion of the first element conductive layer 11ea. Another second element conductive layer 11ebA is provided between the first sensor other-end interconnect 51f and the second partial region 11ob. The other first magnetic layer 11A and another portion of the first nonmagnetic layer 11n are provided between the second partial region 11ob and the other second element conductive layer 11ebA. The second partial region 11ob, the other first magnetic layer 11A, and the other portion of the first nonmagnetic layer 11n are included in another first stacked portion S1A.

In the example of the magnetic sensor 112, the first nonmagnetic layer 11n includes, for example, MgO. The first nonmagnetic layer 11n includes, for example, an insulative material.

The first current Cs1 flows through a current path between the first sensor one-end interconnect 51e and the first sensor other-end interconnect 51f. The current path includes the second element conductive layer 11eb, the first magnetic layer 11, the portion of the first nonmagnetic layer 11n, the first partial region 11oa, the second partial region 11ob, the other portion of the first nonmagnetic layer 11n, the other first magnetic layer 11A, and the other second element conductive layer 11ebA.

In other words, the first electrical resistance R1 includes the electrical resistance of a current flowing through the first magnetic layer 11, the first opposing magnetic layer 11o, and the other first magnetic layer 11A. For example, the first electrical resistance R1 includes an electrical resistance of a current flowing from the first magnetic layer 11 to the other first magnetic layer 11A by way of the first opposing magnetic layer 11o.

For example, the portion where the first partial region 11oa and the first magnetic layer 11 are stacked is used as one current conduction portion. The portion where the second partial region 11ob and the other first magnetic layer 11A are stacked is used as one current conduction portion. These current conduction portions are connected in series. The number of multiple current conduction portions may be three or more.

In such a configuration, the noise can be reduced further. In such a configuration, for example, the volume (the surface area) of the first opposing magnetic layer 11o can be increased. Thereby, the noise can be reduced.

In the magnetic sensors 111 and 112, the first stacked portion S1 is, for example, a TMR (Tunnel Magneto Resistance Effect) element.

Figure 8A:
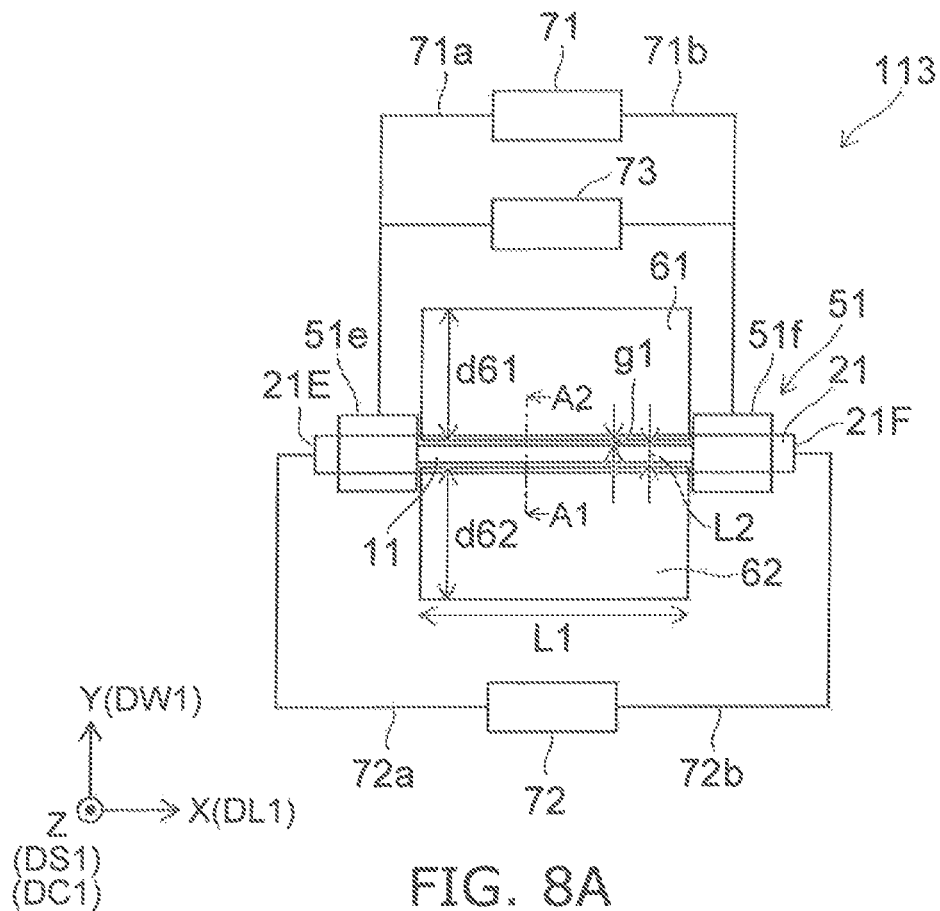
FIG. 8A and FIG. 8B are schematic views illustrating another magnetic sensor according to the first embodiment
Figure 8B:
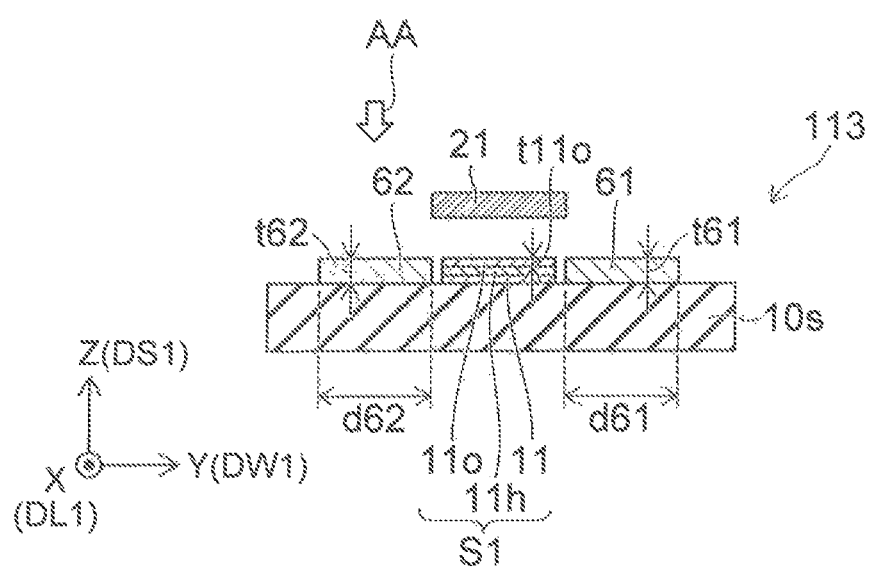

FIG. 8A and FIG. 8B are schematic views illustrating another magnetic sensor according to the first embodiment.

FIG. 8A is a perspective plan view as viewed along arrow AA of FIG. 8B. FIG. 8B is a line A1-A2 cross-sectional view of FIG. 8A. The substrate 10s is not illustrated in FIG. 8A.

In the other magnetic sensor 113 according to the embodiment as shown in FIG. 8A and FIG. 8B, the first sensor element 51 further includes a first magnetic portion 61 and a second magnetic portion 62 in addition to the first magnetic layer 11, the first opposing magnetic layer 11o, the first nonmagnetic layer 11n, and the first interconnect 21.

The first opposing magnetic layer 11o (e.g., the free layer) is positioned between the first magnetic portion 61 and the second magnetic portion 62 in a direction (e.g., the Y-axis direction) crossing a plane (the X-Z plane) including the first stacking direction DS1 (e.g., the Z-axis direction) and the first length direction DL1 (e.g., the X-axis direction).

A thickness t61 along the first stacking direction DS1 (e.g., the Z-axis direction) of the first magnetic portion 61 is thicker than a thickness t11o along the first stacking direction DS1 of the first opposing magnetic layer 11o. A thickness t62 along the first stacking direction DS1 of the second magnetic portion 62 is thicker than the thickness t11o.

The first magnetic portion 61 and the second magnetic portion 62 include, for example, NiFe, etc. The first magnetic portion 61 and the second magnetic portion 62 include, for example, a material having a high permeability. The first magnetic portion 61 and the second magnetic portion 62 include, for example, a soft magnetic material. For example, the signal flux converges easily in the first opposing magnetic layer 11o of the first sensor element 51 due to the high permeability. The first magnetic portion 61 and the second magnetic portion 62 function as, for example, MFCs (Magnetic Flux Concentrators). In a NiFe-based alloy, the permeability is greater than 1000.

The thickness t61 of the first magnetic portion 61 and the thickness t62 of the second magnetic portion 62 each are, for example, not less than 0.1 μm and not more than 10 μm.

As shown in FIG. 8A, the distance between the first magnetic portion 61 and the first opposing magnetic layer 11o is taken as a gap g1. The width (the length in the first width direction DW1) of the first opposing magnetic layer 11o is the same as the length (the second length L2) in the first width direction DW1 of the first magnetic layer 11. The length in the first width direction DW1 of the first magnetic portion 61 is taken as a length d61. The length in the first width direction DW1 of the second magnetic portion 62 is taken as a length d62. The length d62 is the same as the length d61.

In such a case, an amplification factor G of the signal magnetic field Hsig applied to the first opposing magnetic layer 11o has the permeabilities of the first magnetic portion 61 and the second magnetic portion 62 as an upper limit and is represented substantially by the following first formula.

$$G=0.6\times(d61)/(L2+2\times g1) \quad (1)$$

For example, the amplification factor G is about 300 when the second length L2 is 1 μm, the gap g1 is 3 nm, and the length d61 is 0.5 mm. In other words, the sensitivity can be improved to 300 times.

The resolution of the sensing of the signal magnetic field Hsig is dependent on the sizes of the first magnetic portion 61 and the second magnetic portion 62 (i.e., 2×d61). For example, in a sensor for a magnetocardiograph or a magnetoencephalograph, the cell population activity is sensed using a resolution in the range of not less than 0.1 mm and not more than 5 mm. For example, in such an application, an extremely high sensitivity is obtained by using the first magnetic portion 61 and the second magnetic portion 62 recited above.

For example, in the granular TMR element of the reference example, the large saturation magnetic field Hs (e.g., 1 kOe to 10 kOe) that is unique to the element can be reduced to about 50 Oe or less by using the MFC. Conversely, in the embodiment, the saturation magnetic field Hs can be reduced to about 0.1 Oe by using the MFC. As a result, high sensitivity that is at least 100 times that of the granular TMR element of the reference example is obtained. According to the embodiment, for example, the sensing of a micro magnetic field of about 1 picotesia (pT) is possible. According to the embodiment, for example, neuromagnetism or cardiomagnetism can be sensed with high sensitivity.

Second Embodiment

Multiple sensor elements are provided in a second embodiment.

FIG. 9A to FIG. 9D are schematic views illustrating a magnetic sensor according to the second embodiment. FIG.

9A is a perspective plan view. FIG. 9B is a cross-sectional view illustrating a portion of the magnetic sensor 121.

Figure 9A:
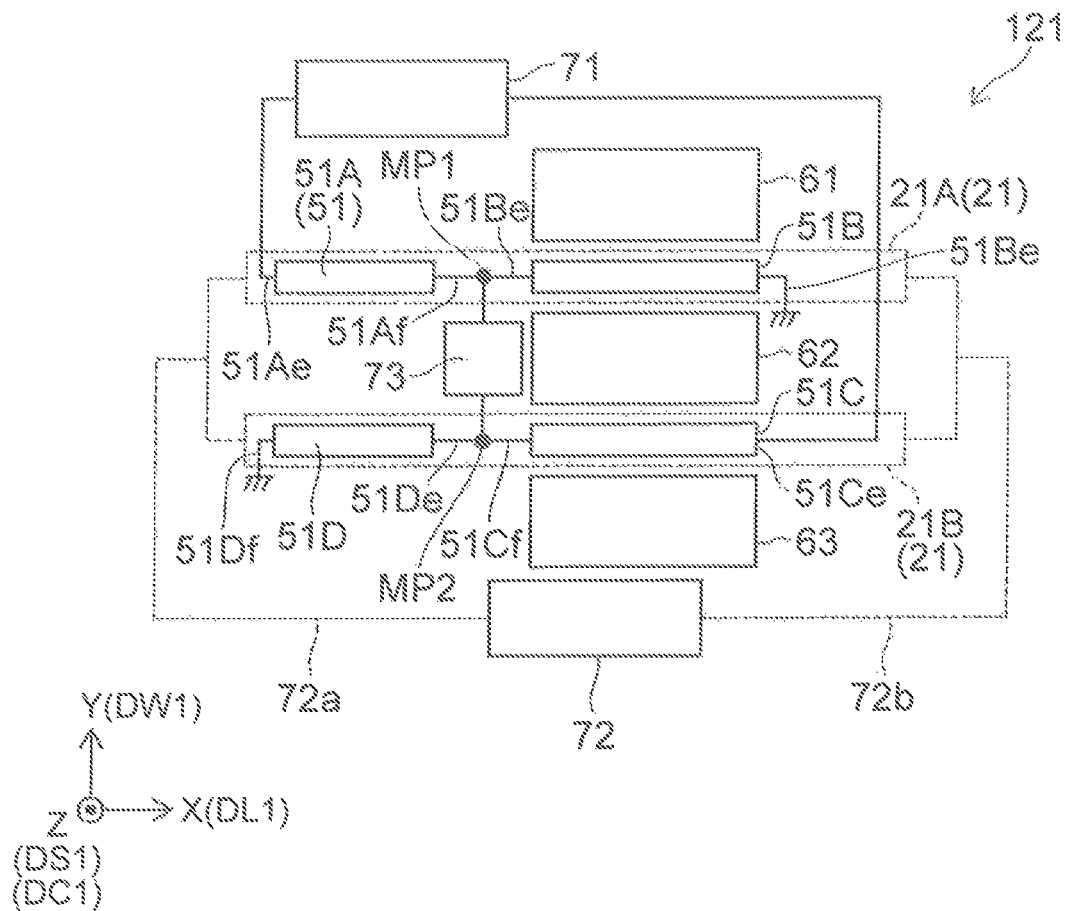
FIG. 9A to FIG. 9D are schematic views illustrating a magnetic sensor according to the second embodiment.
Figures 9B, 9C, 9D:
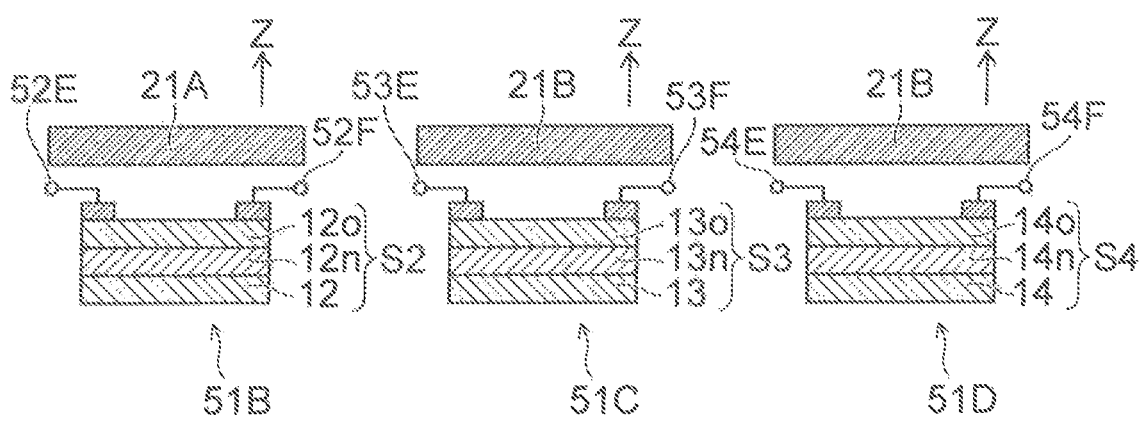

As shown in FIG. 9A, multiple first sensor elements 51 are provided in the magnetic sensor 121 according to the second embodiment. The multiple first sensor elements 51 include sensor elements 51A to 51D.

The sensor element 51A (the first sensor element 51) includes the first magnetic layer 11, the first opposing magnetic layer 11o, and the first nonmagnetic layer 11n. Examples of the first magnetic layer 11, the first opposing magnetic layer 11o, and the first nonmagnetic layer 11n are as described above.

As shown in FIG. 9B, the sensor element 51B includes a second magnetic layer 12, a second opposing magnetic layer 12o, and a second nonmagnetic layer 12n provided between the second magnetic layer 12 and the second opposing magnetic layer 12o. The second magnetic layer 12, the second opposing magnetic layer 12o, and the second nonmagnetic layer 12n are included in a second stacked portion S2.

As shown in FIG. 9C, the sensor element 51C includes a third magnetic layer 13, a third opposing magnetic layer 13o, and a third nonmagnetic layer 13n provided between the third magnetic layer 13 and the third opposing magnetic layer 13o. The third magnetic layer 13, the third opposing magnetic layer 13o, and the third nonmagnetic layer 13n are included in a third stacked portion S3.

As shown in FIG. 9D, the sensor element 51D includes a fourth magnetic layer 14, a fourth opposing magnetic layer 14o, and a fourth nonmagnetic layer 14n provided between the fourth magnetic layer 14 and the fourth opposing magnetic layer 14o. The fourth magnetic layer 14, the fourth opposing magnetic layer 14o, and the fourth nonmagnetic layer 14n are included in a fourth stacked portion S4.

Multiple first interconnects 21 are provided in the example. The multiple first interconnects 21 include interconnects 21A and 21B. As shown in FIG. 9A, the sensor element 51A and the sensor element 51B overlap the interconnect 21A. The sensor element 51C and the sensor element 51D overlap the interconnect 21B.

One end 51Ae of the sensor element 51A is connected to the first circuit 71. Another end 51Af of the sensor element 51A is connected to the third circuit 73 and one end 51Be of the second sensor element 51B. Another end 51Bf of the sensor element 51B is set to, for example, one potential (e.g., the ground potential). One end 51Ce of the sensor element 51C is connected to the first circuit 71. Another end 51Cf of the sensor element 51C is connected to the third circuit 73 and one end 51De of the sensor element 51D. Another end 51Df of the sensor element 51D is set to, for example, one potential (e.g., the ground potential).

The interconnect 21A and the interconnect 21B are connected to the second circuit 72 via the interconnect 72a and the interconnect 72b. The second circuit 72 supplies the alternating current second current Ch1 to the interconnect 21A and the interconnect 21B. In FIG. 9A, the interconnect 21A, the interconnect 21B, the interconnect 72a, and the interconnect 72b are drawn as broken lines for easier viewing of the drawing.

The first magnetic portion 61, the second magnetic portion 62, and a third magnetic portion 63 are provided in the example. The configurations and materials described in reference to the first magnetic portion 61 and the second magnetic portion 62 are applicable to the third magnetic portion 63. The third magnetic portion 63 also is a MFC.

A magnetic layer (e.g., the second opposing magnetic layer 12o) of the sensor element 51B is positioned between the first magnetic portion 61 and the second magnetic portion 62. A magnetic layer (e.g., the third opposing magnetic layer 13o) of the sensor element 51C is positioned between the second magnetic portion 62 and the third magnetic portion 63. On the other hand, a magnetic layer (e.g., the first opposing magnetic layer 11o) of the sensor element 51A is not provided between the first magnetic portion 61 and the second magnetic portion 62. A magnetic layer (e.g., the fourth opposing magnetic layer 14o) of the sensor element 51D is not provided between the second magnetic portion 62 and the third magnetic portion 63.

By such a configuration, the signal magnetic field Hsig that is amplified by the MFCs is applied to the sensor element 51B and the sensor element 51C. Compared to the sensor element 51A and the sensor element 51D, a magnetic field that is at least 10 times greater is applied to the sensor element 51B and the sensor element 51C.

For example, when the signal magnetic field Hsig is zero, the potentials of intermediate points MP1 and MP2 match each other. The resistances of the sensor element 51A and the sensor element 51C change when the signal magnetic field Hsig is applied. Therefore, the potentials of the intermediate points MP1 and MP2 fluctuate in mutually-reverse directions. For example, the intermediate point MP2 is negative when the intermediate point MP1 is positive. For example, the intermediate point MP2 is positive when the intermediate point MP1 is negative. A potential difference occurs between the intermediate point MP1 and the intermediate point MP2 according to the signal magnetic field Hsig. The potential difference is sensed by the third circuit 73. The noise is reduced; and highly-sensitivity sensing is possible.

Figures 10A, 10B:
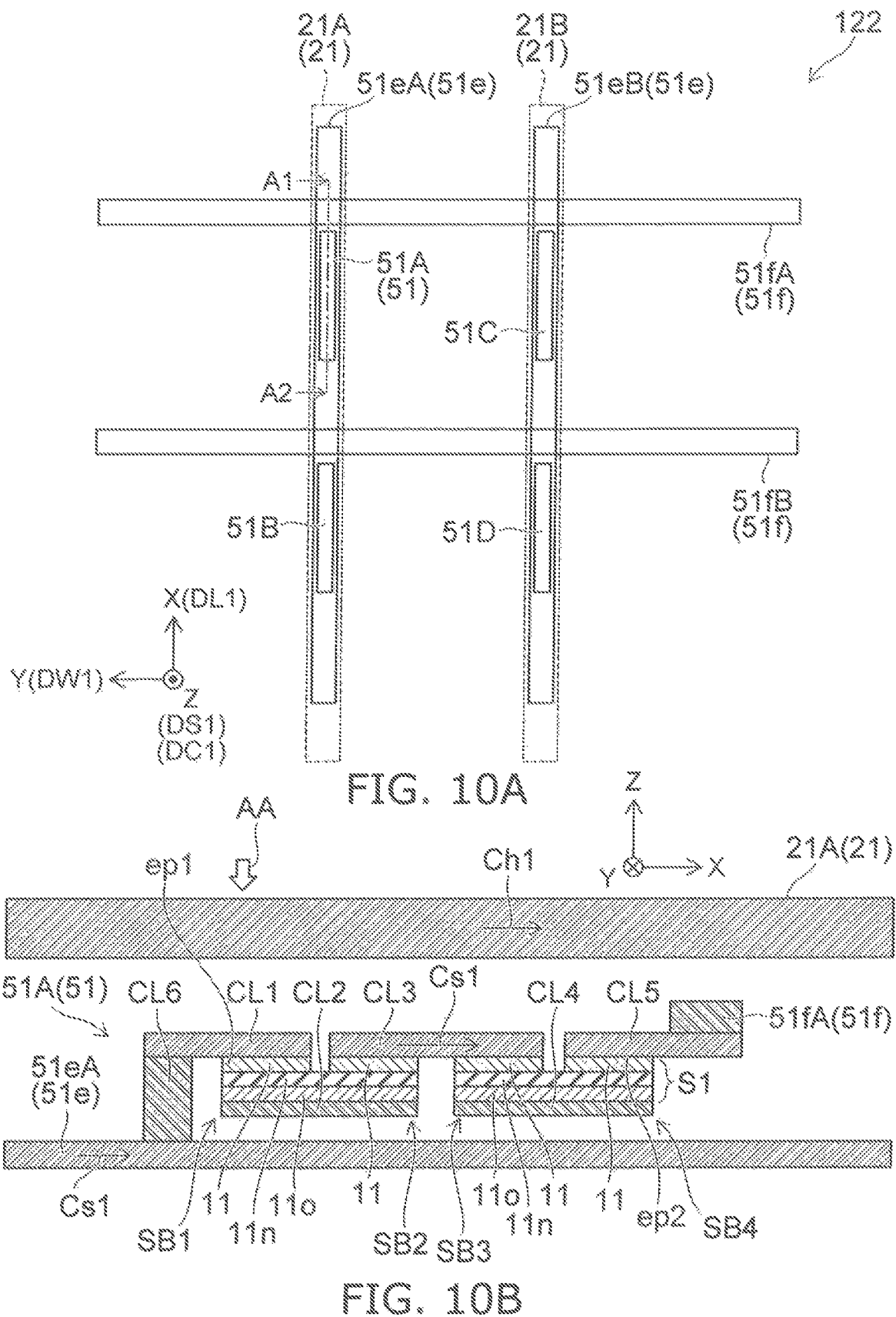
FIG. 10A and FIG. 10B are schematic views illustrating another magnetic sensor according to the second embodiment.

FIG. 10A and FIG. 10B are schematic views illustrating another magnetic sensor according to the second embodiment.

FIG. 10A is a perspective plan view as viewed along arrow AA of FIG. 10B. FIG. 10B is a line A1-A2 cross-sectional view of FIG. 10A.

As shown in FIG. 10A, the magnetic sensor 122 according to the embodiment includes multiple first sensor one-end interconnects 51e (e.g., an interconnect 51eA, an interconnect 51eB, etc.) and multiple first sensor other-end interconnects 51f (e.g., an interconnect 51fA, an interconnect 51fB, etc.).

In the magnetic sensor 122, the multiple first sensor elements 51 (the sensor elements 51A to 51D, etc.) are provided. The multiple first interconnects 21 (the interconnects 21A, 21B, etc.) are provided.

One (e.g., the interconnect 21A) of the multiple first interconnects 21 overlaps the multiple first sensor elements 51 (the sensor elements 51A and 51B) in the first stacking direction DS1 (the Z-axis direction). The multiple first interconnects 21 are arranged in the cross direction (in the example, the Y-axis direction) crossing the first length direction DL1 (in the example, the X-axis direction) and the first stacking direction DS1 (in the example, the Z-axis direction).

The multiple first sensor one-end interconnects 51e extend along the first length direction DL1. The multiple first sensor other-end interconnects 51f extend along the cross direction (in the example, the Y-axis direction) recited above that crosses the first length direction DL1 and the first stacking direction DS1.

As shown in FIG. 10B, one (the interconnect 51eA) of the multiple first sensor one-end interconnects 51e is electrically connected to a first end ep1 of the first sensor element 51 (e.g., the sensor element 51A). One (e.g., the interconnect 51fA) of the multiple first sensor other-end interconnects 51f is electrically connected to a second end ep2 of the first sensor element 51 (e.g., the sensor element 51A).

Thus, one of the multiple first sensor elements 51 is connected to one of the multiple first sensor one-end interconnects 51e and one of the multiple first sensor other-end interconnects 51f. For example, the multiple first sensor one-end interconnects 51e and the multiple first sensor other-end interconnects 51f are connected to the first circuit 71 and the third circuit 73.

The multiple first sensor elements 51 are arranged two-dimensionally along the X-axis direction and the Y-axis direction.

In the example as shown in FIG. 10B, multiple stacked portions (stacked portions SB1 to SB4) are provided in one of the multiple first sensor elements 51. The first magnetic layer 11, the first opposing magnetic layer 11o, and the first nonmagnetic layer 11n are included in each of the stacked portions SB1 to SB4. The stacked portions SB1 to SB4 are connected in series to each other. In the example, one end of the stacked portion SB1 is connected to the interconnect 51eA by a connection layer CL1. The other end of the stacked portion SB1 and one end of the stacked portion SB2 are connected by a connection layer CL2. The other end of the stacked portion SB2 and one end of the stacked portion SB3 are connected by a connection layer CL3. The other end of the stacked portion SB3 and one end of the stacked portion SB4 are connected by a connection layer CL4. The other end of the stacked portion SB4 and the interconnect 51fA are connected by a connection layer CL5. In the example, a connection member CL6 that extends in the Z-axis direction is provided. The connection layer CL1 and the interconnect 51eA are electrically connected by the connection member CL6.

As shown in FIG. 10A, optically transmissive spaces can be provided out of the multiple first sensor one-end interconnects 51e, the multiple first sensor other-end interconnects 51f, and the multiple first interconnects 21. As described below, for example, pixels (optical sensors) of an image sensor may be provided in the optically transmissive spaces. Advanced sensing is possible by using both an optical sensor and the magnetic sensor according to the embodiment.

An example of the configuration of the magnetic sensor 122 will now be described. The length (the first length L1) in the X-axis direction of one first magnetic layer 11 (pinned layer) is 2 μm. The length in the X-axis direction of the entire four first magnetic layers 11 is 12 μm. The number of the multiple stacked portions is four. The length (a second length L2) in the Y-axis direction of the first magnetic layer 11 is 1 μm. The resistance change ratio of one stacked portion is 200%. For example, the current that flows in one first sensor element 51 (sensor element 51A) is 0.2 mA. The resistance (when the resistance is low) of the sensor element 51A is 10 kΩ. The saturation magnetic field Hs of the first opposing magnetic layer 11o is 65 oersteds (Oe). The magnetic thickness of the first opposing magnetic layer 11o is 5 nm·teslas. The Hooge constant of the 1/f noise is $8 \times 10^{-8}$. The frequency (the alternating current frequency fac) of the second current Ch1 flowing in the first interconnect 21 is 10 MHz. It is assumed that the 1/f noise and the thermal noise are the noise sources.

In such a model, the difference of the positive and negative signal voltages in a high frequency domain at the 10 MHz vicinity is sensed as the output. The low frequency fluctuation component is reset or removed. Therefore, the 1/f noise decreases.

For example, a signal magnetic field Hsig of 10 Hz is sensed by the magnetic sensor 122 according to the embodiment. In the embodiment, the noise can be reduced drastically compared to a general TMR sensor in which a spin-valve type linear response is utilized.

For example, in a general micro-sized TMR sensor of about 20 μm utilizing a spin-valve type linear response, a magnetic field of about 100 nT is the limit of the sensing. Conversely, in the embodiment, for example, a micro magnetic field of 0.1 nT to 1 nT can be sensed. Highly-sensitivity sensing is possible.

For example, in the sensing of electric activity of cells cultured on a sensor substrate, the distance between the sensor and the cell is set to 1 μm to 10 μm. In such a case, it is considered that the magnetic field from the cell activity is about 1 nT to 10 nT. According to the magnetic sensor according to the embodiment, the sensing of the activity of the cultured cell is possible.

FIG. 11A to FIG. 11C are schematic views illustrating another magnetic sensor according to the second embodiment.

FIG. 11A is a perspective plan view as viewed along arrow AA of FIG. 11B and FIG. 11C. FIG. 11B is a line E1-E2 cross-sectional view of FIG. 11A. FIG. 11C is a line F1-F2 cross-sectional view of FIG. 11A.

The first sensor element 51 is provided as shown in FIG. 11A. As described above, the first magnetic layer 11 of the first sensor element 51 extends along the first length direction DL1 (in the example, the X-axis direction). A second sensor element 52 is further provided in the magnetic sensor 123. The second sensor element 52 extends along a direction crossing the direction in which the first sensor element 51 extends. A second interconnect 22 is further provided. The second sensor element 52 and the second interconnect 22 will now be described.

As shown in FIG. 11B and FIG. 11C, the second sensor element 52 includes the second magnetic layer 12, the second opposing magnetic layer 12o, and the second nonmagnetic layer 12n. The second nonmagnetic layer 12n is provided between the second magnetic layer 12 and the second opposing magnetic layer 12o. The second magnetic layer 12, the second opposing magnetic layer 12o, and the second nonmagnetic layer 12n are included in the second stacked portion S2.

For example, the second magnetic layer 12, the second opposing magnetic layer 12o, and the second nonmagnetic layer 12n respectively include the materials described in reference to the first magnetic layer 11, the first opposing magnetic layer 11o, and the first nonmagnetic layer 11n.

A second magnetization M2 of the second magnetic layer 12 is aligned with a second length direction DL2. The second length direction DL2 crosses the first length direction DL1. In the example, the second length direction DL2 is aligned with the Y-axis direction.

A second stacking direction DS2 from the second magnetic layer 12 toward the second opposing magnetic layer 12o crosses the second length direction DL2. In the example, the second stacking direction DS2 is aligned with the Z-axis direction.

At least a portion of the second interconnect 22 extends along the second length direction DL2. A second interconnect cross direction DC2 from the second sensor element 52 toward the at least a portion of the second interconnect 22 recited above crosses the second length direction DL2. In the example, the second interconnect cross direction DC2 is aligned with the Z-axis direction. A distance d2 between the second interconnect 22 and the second sensor element 52 may be substantially the same as the distance d1.

The direction in which the second sensor element 52 extends crosses the direction in which the first sensor element 51 extends; and the direction in which the second interconnect 22 extends crosses the direction in which the first interconnect 21 extends. Otherwise, the configuration of the first sensor element 51 is applicable to the second sensor element 52; and the configuration of the first interconnect 21 is applicable to the second interconnect 22.

For example, a second electrical resistance of the second sensor element 52 changes according to the current flowing in the second interconnect 22 and the sensed magnetic field (the signal magnetic field Hsig) applied to the second sensor element 52.

A portion of the second interconnect 22 overlaps the second sensor element 52 in the second interconnect cross direction DC2. The direction of the current flowing in the portion of the second interconnect 22 is aligned with the magnetization direction of the second magnetic layer 12. An alternating-current magnetic field is generated by the current flowing through the second interconnect 22. The alternating-current magnetic field has a component in the width direction of the second sensor element 52 (a direction crossing a plane formed by the second length direction DL2 and the second stacking direction DS2, e.g., the X-axis direction). For example, the characteristics of the change of the second electrical resistance of the second sensor element 52 are similar to the characteristics of the change of the first electrical resistance of the first sensor element 51.

In such a case as well, it is favorable to provide shape anisotropy to the second sensor element 52. As shown in FIG. 11B, the length in the second length direction DL2 of the second magnetic layer 12 is taken as a third length L3. As shown in FIG. 11C, the length in a second width direction DW2 of the second magnetic layer 12 is taken as a fourth length L4. The second width direction DW2 is aligned with the first length direction DL1 (the X-axis direction). The third length L3 is longer than the fourth length L4. For example, the third length L3 is not less than 1.5 times the fourth length L4.

The second sensor element 52 is connected to the first circuit 71. The second interconnect 22 is connected to the third circuit 73. The change of the second electrical resistance of the second sensor element 52 is sensed by the second circuit 72.

For example, the first sensor element 51 can sense the Y-axis direction component of the sensed magnetic field. The second sensor element 52 can sense the X-axis direction component of the sensed magnetic field. The output obtained from the first sensor element 51 (the signal corresponding to the change of the first electrical resistance) and the output obtained from the second sensor element 52 (the signal corresponding to the change of the second electrical resistance) are compared. The direction in the X-Y plane of the signal magnetic field Hsig can be sensed by providing such a first sensor element 51, such a second sensor element 52, such a first interconnect 21, and such a second interconnect 22.

The multiple first sensor elements 51 (the sensor elements 51A to 51D), the multiple second sensor elements 52 (sensor elements 52A to 52D), the multiple first interconnects 21 (the interconnects 21A and 21B), and the multiple second interconnects 22 (interconnects 22A and 22B) are provided in the magnetic sensor 123. The multiple first sensor one-end interconnects 51e (the interconnects 51eA and 51eB), the multiple first sensor other-end interconnects 51f (the interconnects 51fA and 51fB), and multiple second sensor one-end interconnects S2e (an interconnect 52eA and an interconnect 52eB) are further provided.

The multiple first interconnects 21 are arranged in the cross direction (in the example, the Y-axis direction) crossing the first length direction DL1 and the first stacking direction DS1. One of the multiple first interconnects 21 (e.g., the interconnect 21A) overlaps one of the multiple first sensor elements 51 (e.g., the sensor element 51A) in the first stacking direction DS1 (e.g., the Z-axis direction).

The multiple first sensor one-end interconnects 51e extend along the first length direction DL1. One of the multiple first sensor one-end interconnects 51e (e.g., the interconnect 51eA) is electrically connected to the first end ep1 of one of the multiple first sensor elements 51 (the sensor element 51A). The electrical connection is performed by, for example, an interconnect layer (e.g., at least one of the connection layers CL1 to CL5, etc.), a connection member (e.g., the connection member CL6, etc.), etc. The interconnect layers and the connection members may include a portion extending in any direction.

The multiple first sensor other-end interconnects 51f extend along the cross direction (e.g., the Y-axis direction) recited above that crosses the first length direction DL1 and the first stacking direction DS1. One of the multiple first sensor other-end interconnects 51f (e.g., the interconnect 51fA) is electrically connected to the second end ep2 of the one of the multiple first sensor elements 51 recited above (the sensor element 51A). The electrical connection is performed by, for example, an interconnect layer, a connection member, etc. The interconnect layer and the connection member may include a portion extending in any direction.

At least a portion of one of the multiple second interconnects 22 (the interconnects 22A, 22B, etc.) overlaps at least a portion of one of the multiple first sensor other-end interconnects 51f in the first interconnect cross direction Dc1 (in the example, the Z-axis direction) recited above. For example, the interconnect 22A overlaps the interconnect 51fA.

The multiple second sensor one-end interconnects 52e extend along the first length direction DL1. At least a portion of one of the multiple second sensor one-end interconnects 52e is parallel to at least a portion of one of the multiple first sensor one-end interconnects 51e. One of the multiple second sensor one-end interconnects 52e (e.g., 52eA) is electrically connected to a third end ep3 of one (e.g., the sensor element S2A) of the multiple second sensor elements 52 (the sensor elements 52A to 52D). One of the multiple first sensor other-end interconnects 51f (e.g., the interconnect 51fA) is electrically connected to a fourth end ep4 of the one of the multiple second sensor elements 52 recited above (the sensor element 52A). The electrical connection is performed by, for example, an interconnect layer, a connection member (e.g., connection members CL7 and CL8 illustrated in FIG. 11B, etc.), etc. The interconnect layer and the connection member may include a portion extending in any direction.

In the example, the multiple first sensor other-end interconnects 51f are connected to the multiple first sensor elements 51 and connected to the multiple second sensor elements 52. The multiple first sensor other-end interconnects 51f are used by the multiple first sensor elements 51 and the multiple second sensor elements 52.

The multiple first interconnects 21 and the multiple second interconnects 22 are electrically connected to the third circuit 73. The multiple first sensor one-end interconnects 51e, the multiple first sensor other-end interconnects 51f, and the multiple second sensor one-end interconnects 52e are electrically connected to the first circuit 71 and the second circuit 72.

By such a configuration, the distribution in the X-Y plane of the signal magnetic field Hsig in any direction can be sensed with low noise and high sensitivity.

Third Embodiment

A magnetic sensor according to the embodiment is applicable to, for example, a biological cell sensing device, etc.

Figure 12:
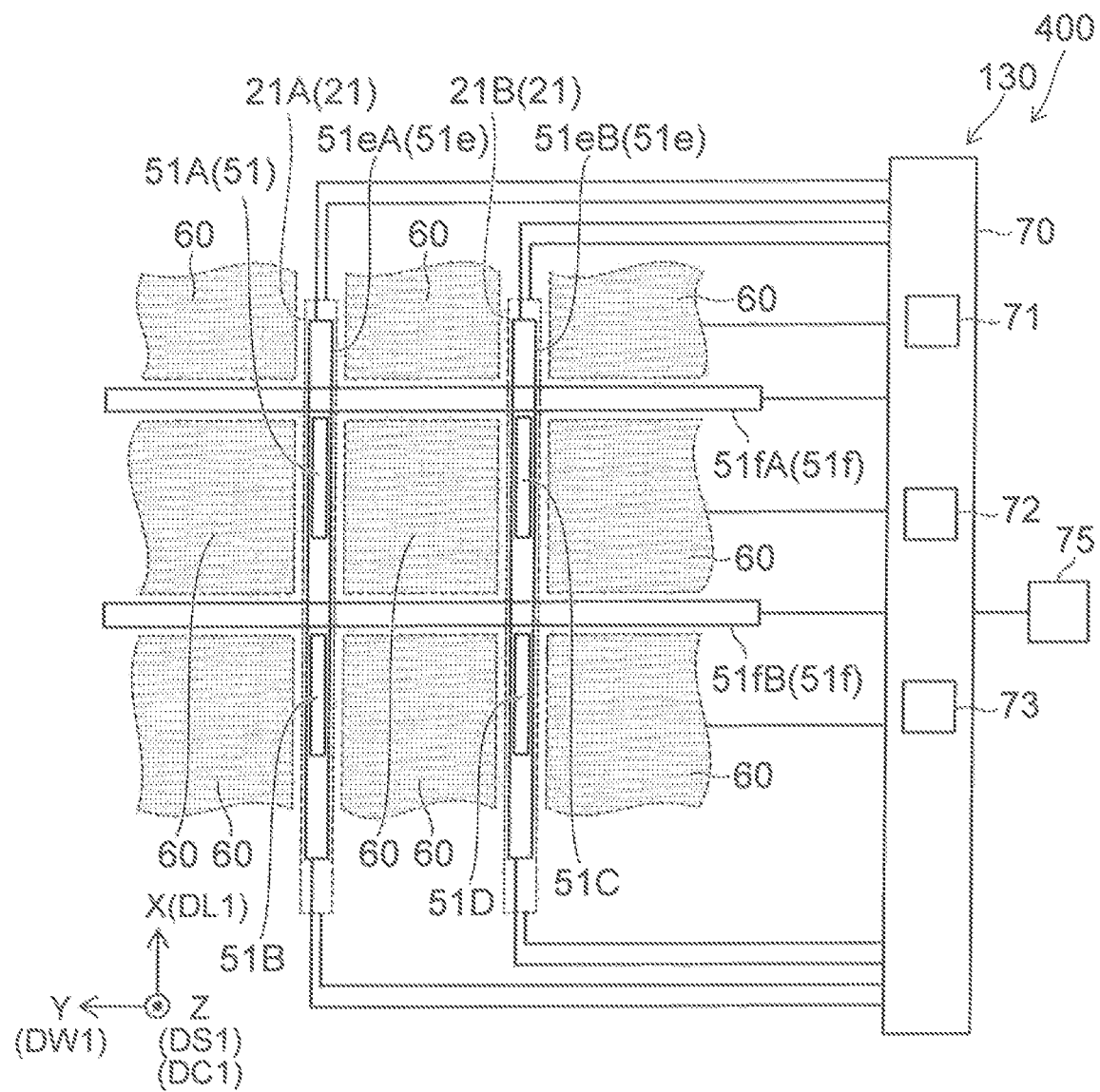
FIG. 12 is a schematic view illustrating the magnetic sensor and the biological cell sensing device according to the third embodiment.

FIG. 12 is a schematic view illustrating the magnetic sensor and the biological cell sensing device according to the third embodiment.

As shown in FIG. 12, the multiple first sensor one-end interconnects 51e, the multiple first sensor other-end interconnects 51f, the multiple first sensor elements 51, and the multiple first interconnects 21 are provided in the magnetic sensor 130 according to the embodiment. These components are similar to those of the magnetic sensor 122; and a description is therefore omitted.

Multiple pixels 60 (e.g., optical sensors) are provided in the magnetic sensor 130. One of the multiple pixels 60 is provided in the gap between the multiple first sensor one-end interconnects 51e and the multiple first sensor other-end interconnects 51f. For example, the pixels 60 correspond to pixels of an image sensor. The image sensor includes, for example, a CMOS sensor, etc. For example, the multiple magnetic sensor elements and the image sensor (the pixels 60) are provided on a substrate. Cells are cultured on the substrate. The magnetic cell activity information and the optical cell activity information of the cultured cells can be sensed. At least a portion of the magnetic cell activity information and at least a portion of the optical cell activity information may be sensed simultaneously. Advanced sensing is possible by using the optical sensor and the sensor using the magnetic field by using the magnetic sensor according to the embodiment.

A circuit portion 70 may be included in the magnetic sensor 130. The circuit portion 70 includes the first circuit 71, the second circuit 72, and the third circuit 73.

The biological cell sensing device 400 according to the embodiment includes the magnetic sensor 130 and a receiver 75. The receiver 75 receives a signal (the information) output from the magnetic sensor 130. The biological cell sensing device 400 senses the state of the biological cells by using the signal (the information). The pixels of the magnetic sensor included in the biological cell sensing device 400 may be omitted. In such a case, the biological cell sensing device 400 senses the state of the biological cells by using the signal (the information) obtained by the magnetic sensor.

Fourth Embodiment

A magnetic sensor according to the embodiment is applicable to, for example, a diagnostic device, etc.

Figure 13:
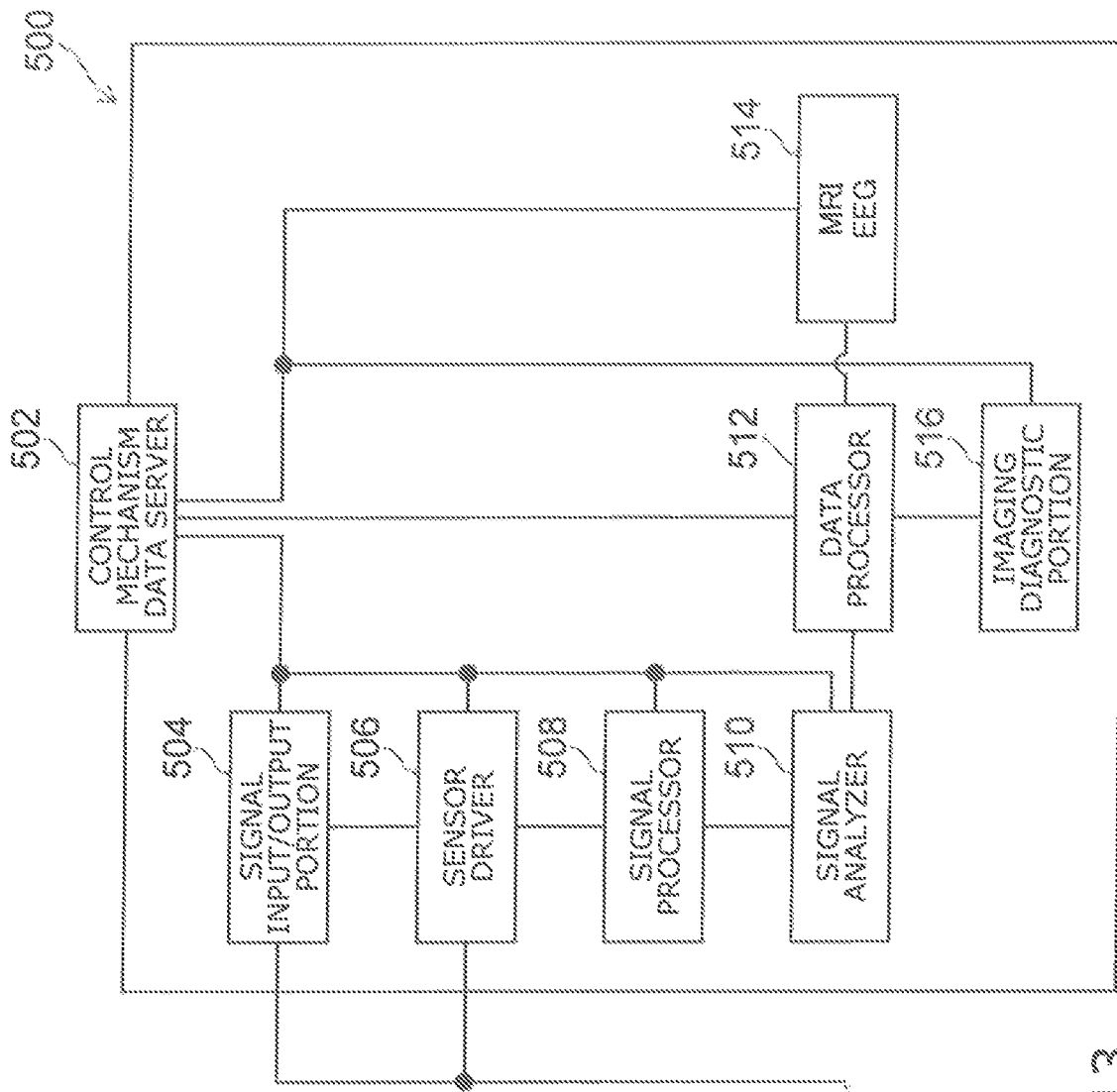
FIG. 13 is a schematic view showing the magnetic sensor and the diagnostic device according to the fourth embodiment.

FIG. 13 is a schematic view showing the magnetic sensor and the diagnostic device according to the fourth embodiment.

As shown in FIG. 13, the diagnostic device 500 includes the magnetic sensor 150. The magnetic sensor 150 includes the magnetic sensors (and the magnetic sensor devices) described in reference to the first embodiment and the second embodiment and modifications of the magnetic sensors (and the magnetic sensor devices).

In the diagnostic device 500, the magnetic sensor 150 is, for example, a magnetoencephalograph device. The magnetoencephalograph device senses a magnetic field generated by cranial nerves. In the case where the magnetic sensor 150 is included in a magnetoencephalograph device, the size of the magnetic element included in the magnetic sensor 150 is, for example, not less than 1 mm but less than 10 mm. The size is, for example, the length including the flux focus path.

As shown in FIG. 13, the magnetic sensor 150 (the magnetoencephalograph device) is mounted to, for example, the head of a human body. The magnetic sensor 150 (the magnetoencephalograph device) includes a sensor portion 301 (the first sensor portion SU1 or the like). The magnetic sensor 150 (the magnetoencephalograph device) may include multiple sensor portions 301 (the first sensor portion SU1, the second sensor portion SU2, etc.). The number of the multiple sensor portions 301 is, for example, about 100 (e.g., not less than 50 and not more than 150). The multiple sensor portions 301 are provided in a base body 302 that is flexible.

The magnetic sensor 150 may include, for example, a circuit for differential sensing, etc. The magnetic sensor 150 may include a sensor other than a magnetic sensor (e.g., a potential terminal, an acceleration sensor, etc.).

The size of the magnetic sensor 150 (the magnetic sensors described in reference to the first embodiment and the second embodiment) is small compared to the size of a conventional SQUID magnetic sensor. Therefore, the mounting of the multiple sensor portions 301 is easy. The mounting of the multiple sensor portions 301 and the other circuits is easy. It is easy for the multiple sensor portions 301 to coexist with the other sensors.

The base body 302 may include, for example, an elastic body such as a silicone resin, etc. For example, the multiple sensor portions 301 are provided in the base body 302 by being linked to each other. For example, the base body 302 can be closely adhered to the head.

An input/output cord 303 of the sensor portion 301 is connected to a signal input/output portion 504 and a sensor driver 506 of the diagnostic device 500. Magnetic field measurement is performed in the sensor portion 301 based on the electrical power from the sensor driver 506 and the control signal from the signal input/output portion 504. The result is input to the signal input/output portion 504. The signal that is obtained by the signal input/output portion 504 is supplied to a signal processor 508. Processing such as, for example, the removal of noise, filtering, amplification, signal calculation, etc., are performed in the signal processor 508. The signal that is processed by the signal processor 508 is supplied to a signal analyzer 510. For example, the signal analyzer 510 extracts a designated signal for magnetoencephalography. For example, signal analysis to match the signal phases is performed in the signal analyzer 510.

The output of the signal analyzer 510 (the data for which the signal analysis has ended) is supplied to a data processor 512. Data analysis is performed in the data processor 512. It is possible to include image data such as, for example, MRI (Magnetic Resonance Imaging), etc., in the data analysis. It is possible to include, for example, scalp potential information such as an EEG (Electroencephalogram), etc., in the data analysis. For example, nerve firing point analysis, inverse analysis, or the like is performed by the data analysis.

For example, the result of the data analysis is supplied to an imaging diagnostic portion 516. Imaging is performed by the imaging diagnostic portion 516. The diagnosis is supported by the imaging.

For example, the series of operations recited above is controlled by a control mechanism 502. For example, necessary data such as preliminary signal data, metadata partway through the data processing, or the like is stored in a data server. The data server and the control mechanism may be integrated.

The diagnostic device 500 according to the embodiment includes the magnetic sensor 150, and a processor that processes the signal obtained from the magnetic sensor 150. The processor includes, for example, at least one of the signal processor 508 or the data processor 512. The processor includes, for example, a computer, etc.

In the magnetic sensor 150 shown in FIG. 13, the sensor portion 301 is mounted to the head of a human body. The sensor portion 301 may be mounted to the chest of the human body. Thereby, a magnetocardiography is possible. For example, the sensor portion 301 may be mounted to the abdomen of a pregnant woman. Thereby, palmoscopy of the fetus can be performed.

It is favorable for the magnetic sensor device including the participant to be mounted inside a shielded room. Thereby, for example, the effects of geomagnetism or magnetic noise can be suppressed.

For example, a mechanism may be provided to locally shield the sensor portion 301 or the measurement section of the human body. For example, a shield mechanism may be provided in the sensor portion 301. For example, the signal analysis or the data processing may be effectively shielded.

In the embodiment, the base body 302 may be flexible or substantially may not be flexible. In the example shown in FIG. 13, the base body 302 is a continuous film that is patterned into a hat-like configuration. The base body 302 may have a net configuration. Thereby, for example, good wearability is obtained. For example, the adhesion of the base body 302 with the human body improves. The base body 302 may have a hard helmet-like configuration.

Figure 14:
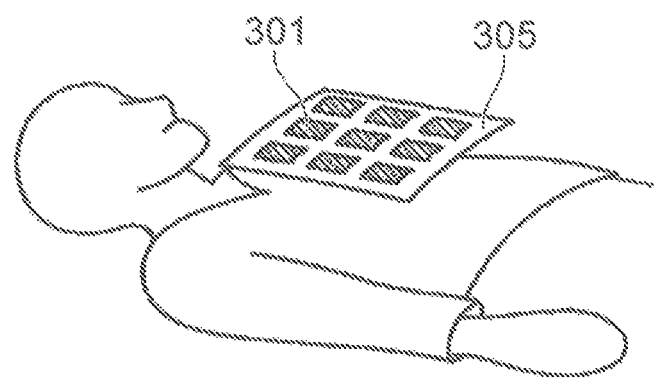
FIG. 14 is a schematic view showing another magnetic sensor according to the fourth embodiment.

FIG. 14 is a schematic view showing another magnetic sensor according to the fourth embodiment.

FIG. 14 is an example of a magnetic sensing instrument. In the example shown in FIG. 14, the sensor portion 301 is provided on a hard base body 305 having a flat plate configuration.

The input and output of the signal obtained from the sensor portion 301 in the example shown in FIG. 14 is similar to the input and output described in reference to FIG. 13. The processing of the signal obtained from the sensor portion 301 in the example shown in FIG. 14 is similar to the processing described in reference to FIG. 13.

The embodiments may include the following configurations (e.g., "technological proposals").

Configuration 1

A magnetic sensor, comprising:

a first sensor element including a first magnetic layer, a first opposing magnetic layer, and a first nonmagnetic layer provided between the first magnetic layer and the first opposing magnetic layer, a first magnetization of the first magnetic layer being aligned with a first length direction, a first stacking direction from the first magnetic layer toward the first opposing magnetic layer crossing the first length direction; and a first interconnect, at least a portion of the first interconnect extending along the first length direction, a first interconnect cross direction crossing the first length direction, the first interconnect cross direction being from the first sensor element toward the at least a portion of the first interconnect, a first electrical resistance of the first sensor element changing according to a current flowing in the first interconnect and a sensed magnetic field applied to the first sensor element.

Configuration 2

The magnetic sensor according to Configuration 1, wherein the first electrical resistance increases when the current flowing in the first interconnect has a positive polarity and the absolute value of the current increases, and the first electrical resistance increases when the current flowing in the first interconnect has a negative polarity and the absolute value of the current increases.

Configuration 3

The magnetic sensor according to Configuration 2, wherein the first electrical resistance when the current does not flow in the first interconnect is not less than 1 times and not more than 1.002 times the minimum value of the first electrical resistance obtained when the current flowing in the first interconnect changes.

Configuration 4

A magnetic sensor, comprising:

a first sensor element including a first magnetic layer, a first opposing magnetic layer, and a first nonmagnetic layer provided between the first magnetic layer and the first opposing magnetic layer, a first stacking direction from the first magnetic layer toward the first opposing magnetic layer crossing the first length direction; and a first interconnect, at least a portion of the first interconnect extending along the first length direction, a first interconnect cross direction crossing the first length direction, the first interconnect cross direction being from the first sensor element toward the at least a portion of the first interconnect, a first electrical resistance of the first sensor element changing according to a current flowing in the first interconnect and a sensed magnetic field applied to the first sensor element, the first electrical resistance increasing when the current flowing in the first interconnect has a positive polarity and the absolute value of the current increases, the first electrical resistance increasing when the current flowing in the first interconnect has a negative polarity and the absolute value of the current increases, the first electrical resistance when the current does not flow in the first interconnect being not less than 1 times and not more than 1.002 times the minimum value of the first electrical resistance obtained when the current flowing in the first interconnect changes.

Configuration 5

A magnetic sensor, comprising:

a first sensor element including a first magnetic layer, a first opposing magnetic layer, and a first nonmagnetic layer provided between the first magnetic layer and the first opposing magnetic layer, a first magnetization of the first magnetic layer being aligned with the first length direction, a first stacking direction from the first magnetic layer toward the first opposing magnetic layer crossing the first length direction; and a first interconnect, at least a portion of the first interconnect extending along the first length direction, a first interconnect cross direction crossing the first length direction, the first interconnect cross direction being from the first sensor element toward the at least a portion of the first interconnect, a first electrical resistance of the first sensor element changing according to a current flowing in the first interconnect and a sensed magnetic field applied to the first sensor element, an orientation of a magnetization of the first opposing magnetic layer being changeable, the first electrical resistance increasing when the current flowing in the first interconnect has a positive polarity and the absolute value of the current increases, the first electrical resistance increasing when the current flowing in the first interconnect has a negative polarity and the absolute value of the current increases, the first electrical resistance when the current does not flow in the first interconnect being not less than 1 times and not more than 1.002 times the minimum value of the first electrical resistance obtained when the current flowing in the first interconnect changes.

Configuration 6

The magnetic sensor according to any one of Configurations 1 to 5, wherein a first length in the first length direction of the first magnetic layer is longer than a second length in the first width direction of the first magnetic layer, and the first width direction crosses a plane including the first stacking direction and the first length direction.

Configuration 7

The magnetic sensor according to any one of Configurations 1 to 6, wherein the first interconnect cross direction is aligned with the first stacking direction.

Configuration 8

The magnetic sensor according to any one of Configurations 1 to 7, wherein the first nonmagnetic layer includes Cu.

Configuration 9

The magnetic sensor according to any one of Configurations 1 to 7, wherein the first sensor element further includes another first magnetic layer and another first nonmagnetic layer, the first opposing magnetic layer is positioned between the first magnetic layer and the other first magnetic layer in the first stacking direction, and the other first nonmagnetic layer is positioned between the other first magnetic layer and the first opposing magnetic layer in the first stacking direction.

Configuration 10

The magnetic sensor according to any one of Configurations 1 to 7, wherein the first sensor element further includes another first magnetic layer, the first opposing magnetic layer includes a first partial region and a second partial region, a portion of the first nonmagnetic layer is positioned between the first magnetic layer and the first partial region, another portion of the first nonmagnetic layer is positioned between the other first magnetic layer and the second partial region, and the first electrical resistance includes an electrical resistance of a current flowing through the first magnetic layer, the first opposing magnetic layer, and the other first magnetic layer.

Configuration 11

The magnetic sensor according to Configuration 9 or 10, wherein the first nonmagnetic layer includes MgO.

Configuration 12

The magnetic sensor according to any one of Configurations 1 to 10, further comprising:

a first circuit electrically connected to the first sensor element, the first circuit supplying a first current to the first sensor element, the first current flowing through a first current path including the first magnetic layer, the first nonmagnetic layer, and the first opposing magnetic layer;

a second circuit electrically connected to the first interconnect, the second circuit supplying a second current to the first interconnect, the second current being alternating current; and a third circuit sensing the change of the first electrical resistance.

Configuration 13

The magnetic sensor according to Configuration 12, wherein the second current has a first frequency, and the third circuit senses an alternating current signal having a frequency in a range including the first frequency.

Configuration 14

The magnetic sensor according to Configuration 12, wherein the third circuit includes a lock-in amplifier.

Configuration 15

The magnetic sensor according to Configuration 12, wherein the second current has a first frequency, and the third circuit includes:

a filter, a signal corresponding to the first electrical resistance being input to the filter, the filter attenuating a signal of a frequency of 2 times the first frequency or more; and a lock-in amplifier, an output of the filter being input to the lock-in amplifier.

Configuration 16

The magnetic sensor according to Configuration 10, further comprising a stacked body, the stacked body including two magnetic layers and a nonmagnetic layer, the nonmagnetic layer being provided between the two magnetic layers, a strength of the sensed magnetic field applied to the stacked body being smaller than a strength of the sensed magnetic field applied to the first sensor element, the third circuit outputting a signal corresponding to a difference between a signal obtained from the stacked body and a signal obtained from the first sensor element.

Configuration 17

The magnetic sensor according to any one of Configurations 1 to 16, wherein the first sensor element further includes a first magnetic portion and a second magnetic portion, the first opposing magnetic layer is positioned between the first magnetic portion and the second magnetic portion in a direction crossing a plane including the first stacking direction and the first length direction, a thickness along the first stacking direction of the first magnetic portion is thicker than a thickness along the first stacking direction of the first opposing magnetic layer, and a thickness along the first stacking direction of the second magnetic portion is thicker than a thickness along the first stacking direction, of the first opposing magnetic layer.

Configuration 18

The magnetic sensor according to any one of Configurations 1 to 17, further comprising:

multiple first sensor one-end interconnects; and multiple first sensor other-end interconnects, the first sensor element being multiply provided, the first interconnect being multiply provided, one of the multiple first interconnects overlapping the multiple first sensor elements in the first stacking direction, the multiple first interconnects being arranged in a cross direction crossing the first length direction and the first stacking direction, the multiple first sensor one-end interconnects extending along the first length direction, one of the multiple first sensor one-end interconnects being electrically connected to a first end of the first sensor element, the multiple first sensor other-end interconnects extending along the cross direction crossing the first length direction and the first stacking direction, one of the multiple first sensor other-end interconnects being electrically connected to a second end of the first sensor element.

Configuration 19

The magnetic sensor according to any one of Configurations 1 to 17, further comprising:

a second sensor element; and a second interconnect, the second sensor element including a second magnetic layer, a second opposing magnetic layer, and a second nonmagnetic layer provided between the second magnetic layer and the second opposing magnetic layer, a second magnetization of the second magnetic layer being aligned with a second length direction, a second stacking direction from the second magnetic layer toward the second opposing magnetic layer crossing the second length direction, the second length direction crossing the first length direction, at least a portion of the second interconnect extending along the second length direction, a second interconnect cross direction crossing the second length direction, the second interconnect cross direction being from the second sensor element toward the at least a portion of the second interconnect, a second electrical resistance of the second sensor element changing according to a current flowing in the second interconnect and the sensed magnetic field applied to the second sensor element.

Configuration 20

The magnetic sensor according to Configuration 19, wherein a third length in the second length direction of the second magnetic layer is longer than a fourth length in the second width direction of the second magnetic layer, and the second width direction is aligned with the first length direction.

Configuration 21

The magnetic sensor according to Configuration 19 or 20, further comprising:

multiple first sensor one-end interconnects;

multiple first sensor other-end interconnects; and multiple second sensor one-end interconnects, the first sensor element being multiply provided, the first interconnect being multiply provided, the multiple first interconnects being arranged in a cross direction crossing the first length direction and the first stacking direction, one of the multiple first interconnects overlapping one of the multiple first sensor elements in the first stacking direction, the multiple first sensor one-end interconnects extending along the first length direction, one of the multiple first sensor one-end interconnects being electrically connected to a first end of the one of the multiple first sensor elements, the multiple first sensor other-end interconnects extending along the cross direction crossing the first length direction and the first stacking direction, one of the multiple first sensor other-end interconnects being electrically connected to a second end of the one of the multiple first sensor elements, the second sensor element being multiply provided, the second interconnect being multiply provided, at least a portion of one of the multiple second interconnects overlapping at least a portion of one of the multiple first sensor other-end interconnects in the first interconnect cross direction, the multiple second sensor one-end interconnects extending along the first length direction, one of the multiple second sensor one-end interconnects being electrically connected to a third end of one of the multiple second sensor elements, one of the multiple first sensor other-end interconnects being electrically connected to a fourth end of the one of the multiple second sensor elements.

Configuration 22

A biological cell sensing device, comprising:

the magnetic sensor according to any one of Configurations 1 to 21; and a receiver receiving a signal output from the magnetic sensor.

Configuration 23

A diagnostic device, comprising:

the magnetic sensor according to any one of Configurations 1 to 21; and a processor processing a signal obtained from the magnetic sensor.

According to the embodiments, a magnetic sensor, a biological cell sensing device, and a diagnostic device can be provided in which the sensing sensitivity can be increased.

In the specification of the application, "perpendicular" and "parallel" refer to not only strictly perpendicular and strictly parallel but also include, for example, the fluctuation due to manufacturing processes, etc. It is sufficient to be substantially perpendicular and substantially parallel.

Hereinabove, exemplary embodiments of the invention are described with reference to specific examples. However, the embodiments of the invention are not limited to these specific examples. For example, one skilled in the art may similarly practice the invention by appropriately selecting specific configurations of components included in magnetic sensors such as magnetic layers, non-magnetic layers, conductive layers, interconnects, circuits, etc., from known art. Such practice is included in the scope of the invention to the extent that similar effects thereto are obtained.

Further, any two or more components of the specific examples may be combined within the extent of technical feasibility and are included in the scope of the invention to the extent that the purport of the invention is included.

Moreover, all magnetic sensors practicable by an appropriate design modification by one skilled in the art based on the magnetic sensors described above as embodiments of the invention also are within the scope of the invention to the extent that the spirit of the invention is included.

Various other variations and modifications can be conceived by those skilled in the art within the spirit of the invention, and it is understood that such variations and modifications are also encompassed within the scope of the invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the Inventions. The accompanying claims and their equivalents are intended to cover such forms or modifications as would fall within the scope and spirit of the invention.

What is claimed is:

1. A magnetic sensor, comprising:
a first sensor element including a first magnetic layer, a first opposing magnetic layer, and a first nonmagnetic layer provided between the first magnetic layer and the first opposing magnetic layer, a first magnetization of the first magnetic layer being aligned with a first length direction, a first stacking direction from the first magnetic layer toward the first opposing magnetic layer crossing the first length direction; and
a first interconnect, at least a portion of the first interconnect extending along the first length direction, a first interconnect cross direction crossing the first length direction, the first interconnect cross direction being from the first sensor element toward the at least a portion of the first interconnect,
a first electrical resistance of the first sensor element changing according to an alternating current flowing in the first interconnect and a sensed magnetic field applied to the first sensor element,
wherein
the first electrical resistance increases when the alternating current flowing in the first interconnect has a positive polarity and the absolute value of the current increases, and
the first electrical resistance increases when the alternating current flowing in the first interconnect has a negative polarity and the absolute value of the current increases,
the first electrical resistance when the alternating current does not flow in the first interconnect is more than 1 times and less than 1.002 times a minimum value of the first electrical resistance obtained when the alternating current flowing in the first interconnect is changed.

2. The sensor according to claim 1, wherein
a first length in the first length direction of the first magnetic layer is longer than a second length in a first width direction of the first magnetic layer, and
the first width direction crosses a plane including the first stacking direction and the first length direction.

3. The sensor according to claim 1, wherein the first interconnect cross direction is aligned with the first stacking direction.

4. The sensor according to claim 1, wherein the first nonmagnetic layer includes Cu.

5. The sensor according to claim 1, wherein
the first sensor element further includes another first magnetic layer and another first nonmagnetic layer,
the first opposing magnetic layer is positioned between the first magnetic layer and the other first magnetic layer in the first stacking direction, and
the other first nonmagnetic layer is positioned between the other first magnetic layer and the first opposing magnetic layer in the first stacking direction.

6. The sensor according to claim 1, wherein
the first sensor element further includes a first magnetic portion and a second magnetic portion,
the first opposing magnetic layer is positioned between the first magnetic portion and the second magnetic portion in a direction crossing a plane including the first stacking direction and the first length direction,
a thickness along the first stacking direction of the first magnetic portion is thicker than a thickness along the first stacking direction of the first opposing magnetic layer, and
a thickness along the first stacking direction of the second magnetic portion is thicker than the thickness along the first stacking direction of the first opposing magnetic layer.

7. The sensor according to claim 1, further comprising:
a plurality of first sensor one-end interconnects; and
a plurality of first sensor other-end interconnects,
a plurality of the first sensor elements being provided,
a plurality of the first interconnects being provided,
one of the plurality of first interconnects overlapping the plurality of first sensor elements in the first stacking direction,
the plurality of first interconnects being arranged in a cross direction crossing the first length direction and the first stacking direction,
the plurality of first sensor one-end interconnects extending along the first length direction,
one of the plurality of first sensor one-end interconnects being electrically connected to a first end of the first sensor element,
the plurality of first sensor other-end interconnects extending along the cross direction crossing the first length direction and the first stacking direction,
one of the plurality of first sensor other-end interconnects being electrically connected to a second end of the first sensor element.

8. The sensor according to claim 1, further comprising:
a second sensor element; and
a second interconnect,
the second sensor element including a second magnetic layer, a second opposing magnetic layer, and a second nonmagnetic layer provided between the second magnetic layer and the second opposing magnetic layer,
a second magnetization of the second magnetic layer being aligned with a second length direction, a second stacking direction from the second magnetic layer toward the second opposing magnetic layer crossing the second length direction,
the second length direction crossing the first length direction,
at least a portion of the second interconnect extending along the second length direction, a second interconnect cross direction crossing the second length direction, the second interconnect cross direction being from the second sensor element toward the at least a portion of the second interconnect,
a second electrical resistance of the second sensor element changing according to an alternating current flowing in the second interconnect and the sensed magnetic field applied to the second sensor element.

9. The sensor according to claim 8, wherein
a third length in the second length direction of the second magnetic layer is longer than a fourth length in a second width direction of the second magnetic layer, and
the second width direction is aligned with the first length direction.

10. The sensor according to claim 8, further comprising:
a plurality of first sensor one-end interconnects;
a plurality of first sensor other-end interconnects; and
a plurality of second sensor one-end interconnects,
a plurality of the first sensor elements being provided, a plurality of the first interconnects being provided,
the plurality of first interconnects being arranged in a cross direction crossing the first length direction and the first stacking direction,
one of the plurality of first interconnects overlapping one of the plurality of first sensor elements in the first stacking direction,
the plurality of first sensor one-end interconnects extending along the first length direction,
one of the plurality of first sensor one-end interconnects being electrically connected to a first end of the one of the plurality of first sensor elements,
the plurality of first sensor other-end interconnects extending along the cross direction crossing the first length direction and the first stacking direction,
one of the plurality of first sensor other-end interconnects being electrically connected to a second end of the one of the plurality of first sensor elements,
a plurality of the second sensor elements being provided,
a plurality of the second interconnects being provided,
at least a portion of one of the plurality of second interconnects overlapping at least a portion of one of the plurality of first sensor other-end interconnects in the first interconnect cross direction,
the plurality of second sensor one-end interconnects extending along the first length direction,
one of the plurality of second sensor one-end interconnects being electrically connected to a third end of one of the plurality of second sensor elements,
one of the plurality of first sensor other-end interconnects being electrically connected to a fourth end of the one of the plurality of second sensor elements.

11. A biological cell sensing device, comprising:
the magnetic sensor according to claim 1; and
a receiver receiving a signal output from the magnetic sensor.

12. A diagnostic device, comprising:
the magnetic sensor according to claim 1; and
a processor processing a signal obtained from the magnetic sensor.

13. A magnetic sensor, comprising:
a first sensor element including a first magnetic layer, a first opposing magnetic layer, and a first nonmagnetic layer provided between the first magnetic layer and the first opposing magnetic layer, a first magnetization of the first magnetic layer being aligned with a first length direction, a first stacking direction from the first magnetic layer toward the first opposing magnetic layer crossing the first length direction; and
a first interconnect, at least a portion of the first interconnect extending along the first length direction, a first interconnect cross direction crossing the first length direction, the first interconnect cross direction being from the first sensor element toward the at least a portion of the first interconnect,
a first electrical resistance of the first sensor element changing according to an alternating current flowing in the first interconnect and a sensed magnetic field applied to the first sensor element,
wherein
the first sensor element further includes another first magnetic layer,
the first opposing magnetic layer includes a first partial region and a second partial region,
a portion of the first nonmagnetic layer is positioned between the first magnetic layer and the first partial region,
another portion of the first nonmagnetic layer is positioned between the other first magnetic layer and the second partial region, and
the first electrical resistance includes an electrical resistance of a current flowing from the first magnetic layer to the other first magnetic layer by way of the first opposing magnetic layer.

14. The sensor according to claim 13, wherein the first nonmagnetic layer includes MgO.

15. The sensor according to claim 13, further comprising a stacked body, the stacked body including two magnetic layers and a nonmagnetic layer, the nonmagnetic layer being provided between the two magnetic layers,
a strength of the sensed magnetic field applied to the stacked body being smaller than a strength of the sensed magnetic field applied to the first sensor element,
the third circuit outputting a signal corresponding to a difference between a signal obtained from the stacked body and a signal obtained from the first sensor element.

16. A magnetic sensor, comprising:
a first sensor element including a first magnetic layer, a first opposing magnetic layer, and a first nonmagnetic layer provided between the first magnetic layer and the first opposing magnetic layer, a first magnetization of the first magnetic layer being aligned with a first length direction, a first stacking direction from the first magnetic layer toward the first opposing magnetic layer crossing the first length direction;
a first interconnect, at least a portion of the first interconnect extending along the first length direction, a first interconnect cross direction crossing the first length direction, the first interconnect cross direction being from the first sensor element toward the at least a portion of the first interconnect;
a first circuit;
a second circuit; and
a third circuit
a first electrical resistance of the first sensor element changing according to an alternating current flowing in the first interconnect and a sensed magnetic field applied to the first sensor element,
the first circuit electrically being connected to the first sensor element, the first circuit supplying a first current to the first sensor element, the first current flowing through a first current path including the first magnetic layer, the first nonmagnetic layer, and the first opposing magnetic layer;
the second circuit being electrically connected to the first interconnect, the second circuit supplying a second current to the first interconnect, the second current being alternating current; and
the third circuit being configured to sense the change of the first electrical resistance.

17. The sensor according to claim 16, wherein
the second current has a first frequency, and
the third circuit senses an alternating current signal having a frequency in a range including the first frequency.

18. The sensor according to claim 16, wherein
the second current has a first frequency, and
the third circuit includes:
a filter, a signal corresponding to the first electrical resistance being input to the filter, the filter attenuating a signal of a frequency of 2 times the first frequency or more; and a lock-in amplifier, an output of the filter being input to the lock-in amplifier.

* * * * *